(12) United States Patent
Dorn, II

(10) Patent No.: US 12,396,968 B2
(45) Date of Patent: Aug. 26, 2025

(54) MITOFUSIN ACTIVATORS HAVING AN ENDOCYCLIC-BONDED CARBONYL GROUP AND METHODS FOR USE THEREOF

(71) Applicant: Gerald W. Dorn, II, Sullivan's Island, SC (US)

(72) Inventor: Gerald W. Dorn, II, Sullivan's Island, SC (US)

( * ) Notice: Subject to any disclaimer, the term of this patent is extended or adjusted under 35 U.S.C. 154(b) by 0 days.

(21) Appl. No.: 18/547,996

(22) PCT Filed: Apr. 4, 2023

(86) PCT No.: PCT/US2023/017479
§ 371 (c)(1),
(2) Date: Oct. 12, 2023

(87) PCT Pub. No.: WO2023/196340
PCT Pub. Date: Oct. 12, 2023

(65) Prior Publication Data
US 2024/0050386 A1    Feb. 15, 2024

Related U.S. Application Data

(60) Provisional application No. 63/327,880, filed on Apr. 6, 2022.

(51) Int. Cl.
| | |
|---|---|
| *A61K 31/165* | (2006.01) |
| *A61K 31/445* | (2006.01) |
| *A61K 31/4465* | (2006.01) |
| *C07C 233/57* | (2006.01) |
| *C07C 237/24* | (2006.01) |

(52) U.S. Cl.
CPC .......... *A61K 31/165* (2013.01); *A61K 31/445* (2013.01)

(58) Field of Classification Search
CPC ............... A61K 31/165; A61K 31/445; A61K 31/4465; C07C 237/24; C07C 233/57; C07C 2601/14
See application file for complete search history.

(56) References Cited

U.S. PATENT DOCUMENTS

| | | | | |
|---|---|---|---|---|
| 8,367,702 B2* | 2/2013 | Onda | ................ | C07D 401/12 546/159 |
| 11,026,904 B2* | 6/2021 | Dorn, II | ............ | A61K 31/4409 |
| 11,141,390 B2* | 10/2021 | Dorn, II | ............ | A61K 31/4468 |
| 2020/0345669 A1* | 11/2020 | Dorn, II | ............ | A61K 31/4196 |

FOREIGN PATENT DOCUMENTS

WO    2019094830 A1    5/2019

OTHER PUBLICATIONS

Shobert et al. DOI: 10.1039/B105745F (Paper) J. Chem. Soc., Perkin Trans. 1, 2001, 2393-2397. (Year: 2001).*
Kumari et al. (J. Med. Chem. 2020, 63, 12290-12358). (Year: 2020).*
Written Opinion and International Search Report from parent PCT application No. PCT/US2023/017479 mailed Aug. 1, 2023.
Dang, X. et al., "Pharmacophore-based design of phenyl-[hydroxycyclohexyl] cycloalkyl-carboxamide mitofusin activators with improved neuronal activity", Journal of medicinal chemistry, 2021, vol. 64, pp. 12506-12524.
Dorn, G. W. et al., "Mitofusin activation enhances mitochondrial motility and promotes neuroregeneration in CMT2A", Neural regeneration research, 2021, vol. 16, No. 11, pp. 2201-2203.
Dang, X. et al., "Discovery of 6-phenylhexanamide derivatives as potent stereoselective mitofusin activators for the treatment of mitochondrial diseases", Journal of medicinal chemistry, 2020, vol. 63, pp. 7033-7051.
Zhang, L.; Dang, X.; Franco, A.; Zhao, H.; Dorn, G.W., II. Piperine Derivatives Enhance Fusion and Axonal Transport of Mitochondria by Activating Mitofusins. Chemistry 2022, 4, 655-668.

(Continued)

*Primary Examiner* — James H Alstrum-Acevedo
*Assistant Examiner* — Chris E Simmons
(74) *Attorney, Agent, or Firm* — Vorys, Sater, Seymour and Pease LLP

(57) ABSTRACT

Compositions capable of promoting mitofusin activation may include a mitofusin activator having a structure represented by

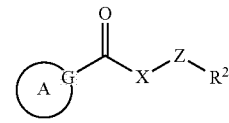

any stereoisomer thereof, or any pharmaceutically acceptable salt thereof. G is N or CH, and A is an optionally substituted 5- or 6-membered cycloalkyl or heterocycloalkyl ring. X is $(CH_2)_3$, $OCH_2CH_2$, $CH_2OCH_2$, $CH_2CH_2O$, Cyc, $CH_2Cyc$, $NR^1(CH_2)_3$, $NR^1OCH_2CH_2$, $NR^1CH_2OCH_2$, $NR^1CH_2CH_2O$, or $NR^1Y$, $R^1$ is H or $C_1$-$C_6$ alkyl, and Cyc is 1,2-cyclopropyl, 1,2-cyclobutyl, 1,3-cyclobutyl, 1,2-cyclopentyl, 1,3-cyclopentyl, 1,2-cyclohexyl, 1,3-cyclohexyl, or 1,4-cyclohexyl. Z is $(CH_2)_n$ or $(CH_2)_{n_1}O(CH_2)_{n_2}$. $R^2$ is an optionally substituted aryl or heteroaryl group. Variable n is an integer ranging from 1 to 5, variable $n_1$ is an integer ranging from 0 to 4, variable $n_2$ is an integer ranging from 0 to 4, and $n_1+n_2=n-1$.

19 Claims, No Drawings

(56) References Cited

OTHER PUBLICATIONS

Dang, Xiawei et al. "Activating mitofusins interrupts mitochondrial degeneration and delays disease progression in SOD1 mutant amyotrophic lateral sclerosis." Human molecular genetics vol. 32,7 (2023): 1208-1222.

* cited by examiner

MITOFUSIN ACTIVATORS HAVING AN ENDOCYCLIC-BONDED CARBONYL GROUP AND METHODS FOR USE THEREOF

STATEMENT REGARDING FEDERALLY SPONSORED RESEARCH OR DEVELOPMENT

This invention was made with government support under grant R$^{42}$NS115184 awarded by the National Institutes of Health. The government has certain rights in the invention.

BACKGROUND

Mitochondrial dysfunction may contribute to various types of neurodegenerative diseases. Defective mitochondrial fusion or fission may be especially problematic in this regard, particularly when imbalanced fusion and fission lead to mitochondrial fragmentation. Among the many neurodegenerative diseases in which mitochondrial dysfunction has been implicated include, for example, Charcot-Marie-Tooth disease, amyotrophic lateral sclerosis (ALS), and Huntington's disease.

Mitochondrial fusion is initiated by outer mitochondrial membrane-embedded mitofusin (MFN) proteins whose extra-organelle domains extend across cytosolic space to interact with counterparts on neighboring mitochondria. The physically linked organelles create oligomers of varying sizes. Mitofusins subsequently induce outer mitochondrial membrane fusion mediated by catalytic GTPase. Aberrant mitofusin activity is believed to be a primary contributor to mitochondrial-based neurodegenerative diseases. For these reasons, mitofusins are attractive targets for drug discovery.

Although several chemical entities have been found to target mitofusins, most have failed to display pharmacokinetic properties compatible with in vivo use. U.S. Patent Application Publications 2020/0345668 and 2020/0345669 describe various 6-phenylhexanamide compounds and structural variants thereof that are capable of activating mitofusins, have an acceptable pharmacokinetic profile, and demonstrate tendency toward blood-brain barrier partitioning, as evidenced by PAMPA (passive artificial blood brain barrier membrane permeability assay) values.

BRIEF DESCRIPTION OF THE DRAWINGS

Not applicable.

DETAILED DESCRIPTION

The present disclosure generally relates to mitofusin activation, and more specifically, compositions comprising mitofusin activators containing a terminal cycloalkyl or heterocycloalkyl group, in which an endocyclic atom is bonded to carbonyl group.

As discussed above, various 6-phenylhexanamide compounds are potent mitofusin activators that may have good pharmacokinetic properties. N-(4-Hydroxycyclohexyl)-6-phenylhexanamide (Formula 1) is a representative example of a mitofusin activator within this class of compounds.

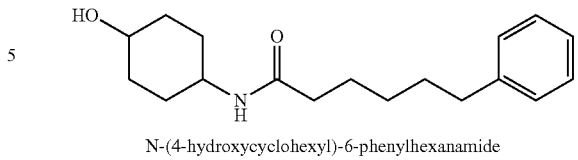

N-(4-hydroxycyclohexyl)-6-phenylhexanamide

As described herein, there is a surprising degree of tolerance for the manner in which a cyclic moiety may be bonded to the carbonyl group of a mitofusin activator. Namely, instead of bonding the cyclic moiety to the carbonyl group via an exocyclic nitrogen atom, as in Formula 1, the cyclic moiety may be bonded directly to the carbonyl group by an endocyclic atom (e.g., an endocyclic nitrogen atom or an endocyclic carbon atom), while still preserving strong mitofusin activation properties. Further surprisingly, by bonding the cyclic moiety to the carbonyl group in the foregoing manner, considerable structural diversity may be tolerated in the linker appended to the carbonyl group, including greater variability in the length of the linker than may be feasible for analogues of Formula 1. By bonding the carbonyl group to an endocyclic atom, improved pharmacokinetic properties may be realized in some instances.

Accordingly, the present disclosure provides compositions comprising a mitofusin activator, any stereoisomer thereof, or any pharmaceutically acceptable salt thereof having a structure represented by Formula 2.

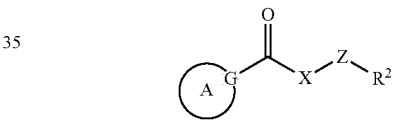

In Formula 2, G is N or CH, and A is an optionally substituted 5- or 6-membered cycloalkyl or heterocycloalkyl ring. X is $(CH_2)_3$, $OCH_2CH_2$, $CH_2OCH_2$, $CH_2CH_2O$, Cyc, $CH_2Cyc$, $NR^1(CH_2)_3$, $NR^1OCH_2CH_2$, $NR^1CH_2OCH_2$, $NR^1CH_2CH_2O$, or $NR^1Cyc$. $R^1$ is H or $C_1$-$C_6$ alkyl. Cyc is 1,2-cyclopropyl, 1,2-cyclobutyl, 1,3-cyclobutyl, 1,2-cyclopentyl, 1,3-cyclopentyl, 1,2-cyclohexyl, 1,3-cyclohexyl, or 1,4-cyclohexyl. Z is $(CH_2)_n$ or $(CH_2)_{n_1}O(CH_2)_{n_2}$, wherein n is an integer ranging from 1 to 5, $n_1$ is an integer ranging from 0 to 4, $n_2$ is an integer ranging from 0 to 4, and $n_1+n_2=n-1$. $R^2$ is an optionally substituted aryl or heteroaryl group, preferably an optionally substituted phenyl group in any embodiment.

In any embodiment herein, the variables may be selected such that G is not CH when X is $CH_2$, Cyc, or $CH_2Cyc$.

The 5- or 6-membered cycloalkyl or heterocycloalkyl ring or the optionally substituted aryl or heteroaryl group in Formula 2 may be optionally substituted at any position by one or more of the following groups: amine, alkylamine, amide, alkylamide, alkoxy, aryloxy, hydroxyalkyl, azo, halogen (F, Cl, Br, I), $C_{1-8}$ alkyl, $C_1$-$C_8$ carbonyl (acyl), carboxylic acids or carboxylic esters, cyano, $C_{3-8}$ cycloalkyl, $C_{3-8}$ heteroaryl, $C_{3-8}$ heterocyclyl, $C_6$-$C_{10}$ aryl, hydroxy, thiol, thioether, sulfoxide, sulfone, and sulfonamide, some of which may be optionally further substituted with acetamide, alkoxy, amino, azo, Br, $C_{1-8}$ alkyl, carbonyl, carboxyl, cyano, $C_{3-8}$ cycloalkyl, $C_{3-8}$ heteroaryl, $C_{3-8}$ heterocyclyl, hydroxy, halogen (F, Cl, Br, I), indole, nitrile, phenyl, sulfoxide, sulfone, sulfonamide, and/or thiophene. Heterocyclyl groups may contain one or more N, O, or S atoms within their ring structure. Any alkyl or cycloalkyl group may be optionally substituted with one or more heteroatoms or heteroatom-containing groups, either within the carbon chain or ring, or as a side chain group.

Suitable aryl or heteroaryl groups that may define $R^2$ include, but are not limited to, any of phenyl, naphthyl, anthracenyl, phenanthrenyl, indenyl, tetrahydronaphthyl, benzofuranyl, benzothienyl, indolyl, benzopyrazolyl, coumarinyl, isocumarinyl, isoquinolinyl, pyrrolyl, pyrrolidinyl, thienyl, furanyl, thiazolyl, imidazolyl, pyrazolyl, triazolyl, quinolinyl, pyrimidinyl, pyridinyl, pyridonyl, pyrazinyl, pyridazinyl, oxazolyl, isothiazolyl, isoxazolyl, tetrazolyl, or any isomer thereof. Any of these aryl or heteroaryl groups may be optionally substituted as further specified above.

In any of the mitofusin activators described herein, $R^2$ may be an optionally substituted phenyl group. The phenyl group may be optionally substituted by one or more of the following entities: amine, alkylamine, amide, alkylamide, alkoxy, aryloxy, hydroxyalkyl, azo, halo (F, Cl, Br, I), $C_{1-8}$ alkyl, $C_1$-$C_8$ carbonyl (acyl), carboxylic acids or carboxylic esters, cyano, $C_{3-8}$ cycloalkyl, $C_{3-8}$ heteroaryl, $C_{3-8}$ heterocyclyl, $C_6$-$C_{10}$ aryl, hydroxy, thiol, thioether, sulfoxide, sulfone, and sulfonamide. Any alkyl or cycloalkyl group may be optionally substituted with one or more heteroatoms or heteroatom-containing groups, either within the carbon chain or ring, or as a side chain group. The optional substitutions upon the phenyl group may be present at any available phenyl ring position. 0, 1, 2, 3, 4 or 5 optional substitutions may be present.

In some examples, the 5- or 6-membered cycloalkyl or heterocycloalkyl ring may be selected from among the following groups, any of which may further bear an optional substitution at any open ring position.

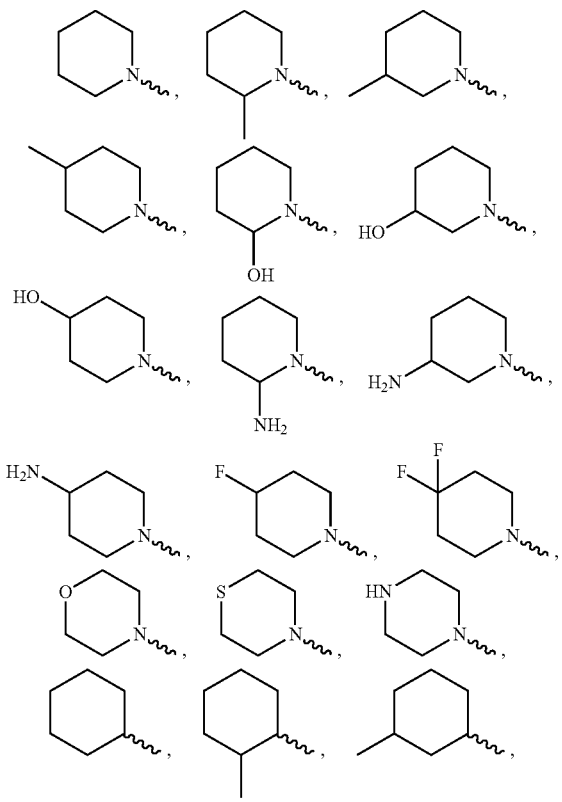

In more specific examples, the 5- or 6-membered cycloalkyl or heterocycloalkyl may be an optionally substituted piperidinyl, piperazinyl, morpholinyl, pyrroldinyl, cyclopentyl, or cyclohexyl group. In some or other examples, the 5- or 6-membered cycloalkyl or heterocycloalkyl may be an optionally substituted piperidinyl, piperazinyl, morpholinyl, or cyclohexyl group.

In some or other still more specific examples, G may be N and A may represent an optionally substituted piperidinyl, piperazinyl, morpholinyl, or pyrrolidinyl group. Such mitofusin activators may have a structure represented by Formula 3.

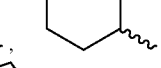

Formula 3

In Formula 3, J is a bond, CH(hal), C(hal)$_2$, CHOR$^3$, CHR$^4$, CHNR$^4$R$^5$, O, or NR$^4$, and Q is an optional substitution, as specified above. For the variables in Formula 3, hal is a halogen (F, Cl, Br, I), $R^3$ is H or $C_1$-$C_6$ alkyl, and $R^4$ and $R^5$ are independently H, $C_1$-$C_6$ alkyl, or $C_1$-$C_6$ acyl. In still more specific examples, G may be N and A may represent an optionally substituted piperidinyl, piperazinyl, or morpholinyl group, wherein J is CH(hal), C(hal)$_2$, CHOR$^3$, CHR$^4$, CHNR$^4$R$^5$, O, or NR$^4$, Q is an optional substitution, and the variables are specified as above.

In some examples, A may represent an optionally substituted piperidinyl, piperazinyl, morpholinyl, or pyrrolidinyl group as defined in Formula 3, and X may be (CH$_2$)$_3$, 1,2-cyclopropyl, 1,2-cyclobutyl, or 1,3-cyclobutyl, wherein Z and $R^2$ may be defined as above. In some examples, A may represent an optionally substituted piperidinyl, piperazinyl, or morpholinyl group, and X may be (CH$_2$)$_3$, 1,2-cyclopropyl, 1,2-cyclobutyl, or 1,3-cyclobutyl, wherein Z and $R^2$ may be defined as above. In more particular examples of any of the foregoing mitofusin activators, Z may be (CH$_2$)$_n$ or $O(CH_2)_{n-1}$, wherein n is an integer ranging from 2 to 5. In any of the foregoing mitofusin activators, $R^2$ may represent an optionally substituted phenyl group.

In some examples of the mitofusin activators defined by Formula 3, A may represent an optionally substituted piperidinyl group, in which J is $CHOR^3$ or $CHR^4$. In still more particular examples of any of the foregoing, A may be 4-hydroxypiperidinyl.

In some examples, A may represent an optionally substituted piperidinyl, piperazinyl, morpholinyl, or pyrrolidinyl group as defined in Formula 3, X may be $OCH_2CH_2$, $CH_2OCH_2$, $CH_2CH_2O$, or $CH_2Cyc$, wherein Cyc is 1,2-cyclopropyl, 1,2-cyclobutyl, or 1,3-cyclobutyl, and Z and $R^2$ may be defined as above. In more particular examples of such mitofusin activators, Z may be $(CH_2)_n$ or $O(CH_2)_{n-1}$, wherein n is an integer ranging from 2 to 5, provided that X and Z are not simultaneously $CH_2CH_2O$ and $O(CH_2)_{n-1}$, respectively. In still more particular examples of such mitofusin activators, A may be an optionally substituted piperidinyl group, in which J is $CHOR^3$ or $CHR^4$. In still more particular examples of any of the foregoing, A may be 4-hydroxypiperidinyl.

In some examples, A may be an optionally substituted piperidinyl, piperazinyl, morpholinyl, or pyrrolidinyl as defined in Formula 3, X may be 1,2-cyclopentyl, 1,3-cyclopentyl, 1,2-cyclohexyl, 1,3-cyclohexyl, or 1,4-cyclohexyl, and Z and $R^2$ may be defined as above. In more particular examples of such mitofusin activators, Z may be $(CH_2)_n$ or $O(CH_2)_{n-1}$, wherein n is an integer ranging from 2 to 5. In still more particular examples of such mitofusin activators, A may represent an optionally substituted piperidinyl group, in which J is $CHOR^3$ or $CHR^4$. In still more particular examples of any of the foregoing, A may be 4-hydroxypiperidinyl.

In more specific examples, the mitofusin activators disclosed herein may have structures represented by any of Formulas 4-6 below.

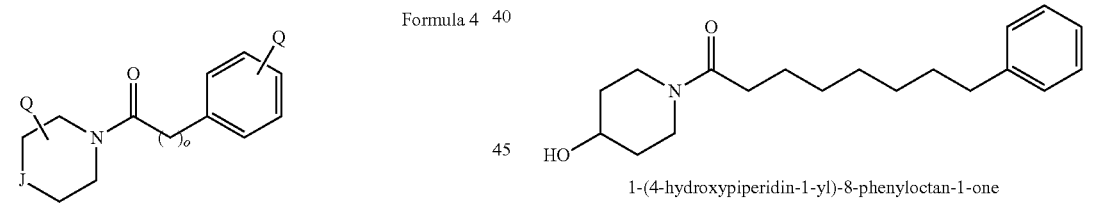

Formula 4

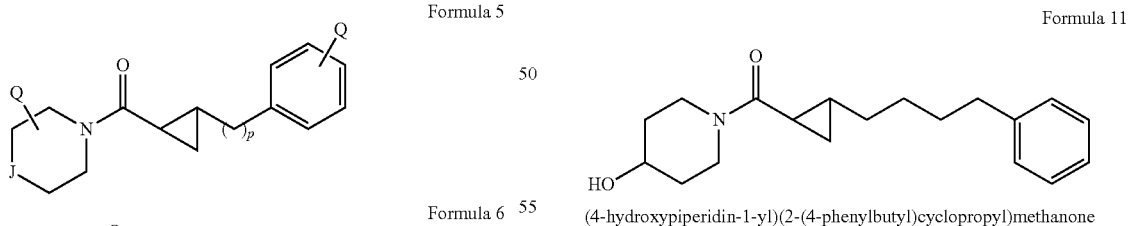

Formula 5

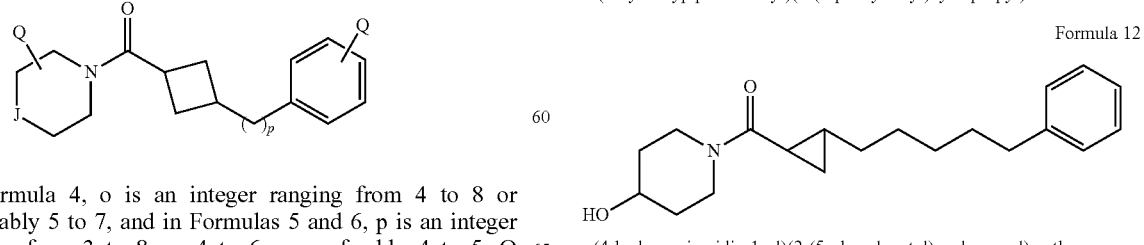

Formula 6

In Formula 4, o is an integer ranging from 4 to 8 or preferably 5 to 7, and in Formulas 5 and 6, p is an integer ranging from 3 to 8, or 4 to 6, or preferably 4 to 5. Q represents one or more optional substitutions upon the phenyl group or the 5- or 6-membered heterocyclic ring, wherein each Q, if present, may be independently selected. In some examples, the 5- or 6-membered heterocyclic ring may be an optionally substituted piperidinyl, piperazinyl, or morpholinyl group. The other variables are defined as above.

In still more specific examples, the mitofusin activators may have structures represented by Formulas 7 to 14 below or any stereoisomer thereof.

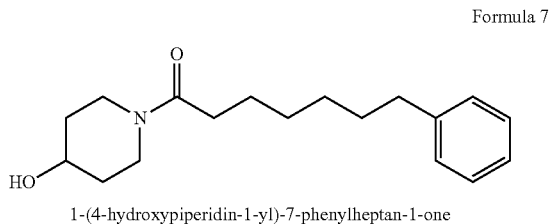

Formula 7

1-(4-hydroxypiperidin-1-yl)-7-phenylheptan-1-one

Formula 8

HO 1-(3-hydroxypiperidin-1-yl)-7-phenylheptan-1-one

Formula 9

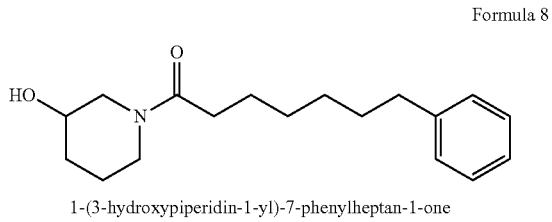

1-(4-hydroxypiperidin-1-yl)-6-phenylhexan-1-one

Formula 10

1-(4-hydroxypiperidin-1-yl)-8-phenyloctan-1-one

Formula 11

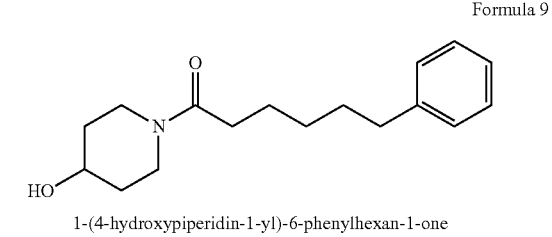

(4-hydroxypiperidin-1-yl)(2-(4-phenylbutyl)cyclopropyl)methanone

Formula 12

(4-hydroxypiperidin-1-yl)(2-(5-phenylpentyl)cyclopropyl)methanone

Formula 13

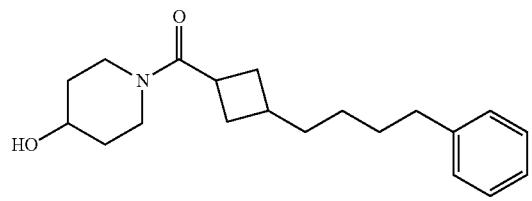

(4-hydroxypiperidin-1-yl)(3-(4-phenylbutyl)cyclobutyl)methanone

Formula 14

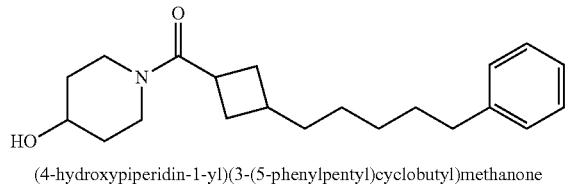

(4-hydroxypiperidin-1-yl)(3-(5-phenylpentyl)cyclobutyl)methanone

In some examples, A may be an optionally substituted piperidinyl, piperazinyl, morpholinyl, or pyrrolidinyl as defined in Formula 3, X may be $NR^1(CH_2)_3$ or X may be $NR^1(CH_2)_3$, $NR^1(1,2$-cyclopropyl), $NR^1(1,2$-cyclobutyl), or $NR^1(1,3$-cyclobutyl), and Z and $R^2$ may be defined as above. In more specific examples, $R^1$ may be H in any of the foregoing. In more particular examples of such mitofusin activators, Z may be $(CH_2)_n$ or $O(CH_2)_{n-1}$, wherein n is an integer ranging from 1 to 4. In more specific examples, X may be $NR^1(CH_2)_3$, Z may be $(CH_2)_n$, and n is an integer ranging from 1 to 4, preferably wherein $R^1$ may be H.

In still more particular examples of any of the foregoing, A may represent an optionally substituted piperidinyl group, in which J is $CHOR^3$ or $CHR^4$. In still more particular examples, A may be 4-hydroxypiperidinyl.

In some examples, A may represent an optionally substituted piperidinyl, piperazinyl, morpholinyl, or pyrrolidinyl group as defined in Formula 3, X may be $NR^1OCH_2CH_2$, $NR^1CH_2OCH_2$, $NR^1CH_2CH_2O$, or $NR^1Cyc$, wherein Cyc is 1,2-cyclopropyl, 1,2-cyclobutyl, or 1,3-cyclobutyl, and Z and $R^2$ may be defined as above. In some embodiments, $R^1$ may be H in any of the foregoing. In more particular examples of such mitofusin activators, Z may be $(CH_2)_n$ or $O(CH_2)_{n-1}$, wherein n is an integer ranging from 1 to 4, provided that X and Z are not simultaneously $NR^1CH_2CH_2O$ and $O(CH_2)_{n-1}$, respectively. In more particular examples of any of the foregoing, A may represent an optionally substituted piperidinyl group, in which J is $CHOR^3$ or $CHR^4$. In still more particular examples, A may be 4-hydroxypiperidinyl.

In some embodiments, A may represent an optionally substituted piperidinyl, piperazinyl, morpholinyl, or pyrrolidinyl group as defined in Formula 3, X may be $NR^1(1,2$-cyclopentyl), $NR^1(1,3$-cyclopentyl), $NR^1(1,2$-cyclohexyl), $NR^1(1,3$-cyclohexyl), or $NR^1(1,4$-cyclohexyl), and Z and $R^2$ may be defined as above. In some embodiments, $R^1$ may be H in any of the foregoing. In more particular examples of such mitofusin activators, Z may be $(CH_2)_n$ or $O(CH_2)_{n-1}$, wherein n is an integer ranging from 1 to 4. In more particular examples of any of the foregoing, A may represent an optionally substituted piperidinyl group, in which J is $CHOR^3$ or $CHR^4$. In still more particular examples, A may be 4-hydroxypiperidinyl.

In more specific examples, the mitofusin activators disclosed herein may have structures represented by any of Formulas 15-17 below.

Formula 15

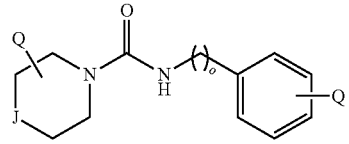

Formula 16

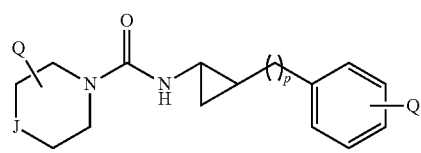

Formula 17

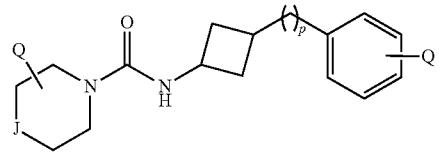

In Formula 15, o is an integer ranging from 5 to 7 or 4 to 6, and in Formulas 16 and 17, p is an integer ranging from 4 to 6 or 3 to 5. Q represents one or more optional substitutions upon the phenyl group or the 5- or 6-membered heterocyclic ring, wherein each Q, if present, may be independently selected. In some examples, the 5- or 6-membered heterocyclic ring may be an optionally substituted piperidinyl, piperazinyl, or morpholinyl group. The other variables are defined as above.

In still more specific examples, the mitofusin activators may have a structure represented by Formula 18 below or any stereoisomer thereof.

Formula 18

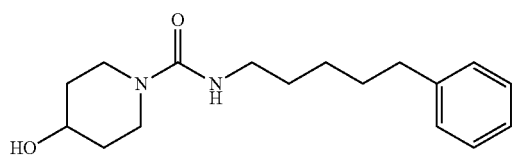

4-hydroxy-N-(5-phenylpentyl)piperidine-1-carboxamide

In other examples of the mitofusin activators disclosed herein, the 5- or 6-membered cycloalkyl or heterocycloalkyl may be an optionally substituted piperidinyl, pyrrolidinyl, tetrahydropyranyl, tetrahydrofuranyl, cyclopentyl, or cyclohexyl group when G is CH. Preferably, A may represent an optionally substituted cyclopentyl or cyclohexyl group. Such mitofusin activators may have a structure represented by Formula 19 or any stereoisomer thereof.

Formula 19

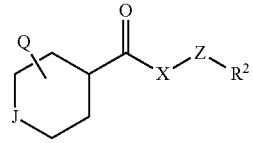

In Formula 19, J is a bond, CH(hal), C(hal)$_2$, $CHOR^3$, $CHR^4$, $CHNR^4R^5$, O, or $NR^4$, and Q is an optional substitution, as specified above. In Formula 19, hal is a halogen (F, Cl, Br, I), $R^3$ is H or $C_1-C_6$ alkyl, and $R^4$ and $R^5$ are independently H, $C_1-C_6$ alkyl, or $C_1-C_6$ acyl. In some embodiments, J is not a bond, O, or $NR^4$, such that A represents an optionally substituted cyclohexyl group. Preferably, J may be $CHOR^3$ or $CHR^4$. In some examples, A may represent a 4-hydroxycyclohexyl group, and the other variables may be specified as above.

In some examples, A may represent an optionally substituted cyclohexyl group defined as in Formula 19, and X may be $NR^1(CH_2)_3$, $NR^1(1,2$-cyclopropyl), $NR^1(1,2$-cyclobutyl), or $NR^1(1,3$-cyclobutyl). $R^1$ may be H or $C_1-C_6$ alkyl in the foregoing, and Z and $R^2$ may be defined as above. In more particular examples of such mitofusin activators, Z may be $(CH_2)_n$ or $O(CH_2)_{n-1}$, wherein n is an integer ranging from 2 to 4. $R^1$ may be H in various examples of such mitofusin activators. In some examples, X may be $NR^1(CH_2)_3$, Z may be $(CH_2)_n$, and n is an integer ranging from 2 to 4. In some examples, X may be $NR^1(1,2$-cyclopropyl), $NR^1(1,2$-cyclobutyl), or $NR^1(1,3$-cyclobutyl), Z may be selected from $(CH_2)_n$ and $O(CH_2)_{n-1}$, and n is an integer ranging from 2 to 4. In more particular examples of any of the foregoing, A may represent an optionally substituted cyclohexyl group, in which J is $CHOR^3$ or $CHR^4$. In still more particular examples of any of the foregoing, A may be 4-hydroxycyclohexyl.

In some examples, A may represent an optionally substituted cyclohexyl group defined as in Formula 19 and specified, and X may be $NR^1OCH_2CH_2$, $NR^1CH_2OCH_2$, or $NR^1CH_2CH_2O$. $R^1$ may be H or $C_1-C_6$ alkyl, and Z and $R^2$ may be defined as above. $R^1$ may be H any examples of such mitofusin activators. In more particular examples of such mitofusin activators, Z may be $(CH_2)_n$ or $O(CH_2)_{n-1}$, wherein n is an integer ranging from 2 to 4, provided that X and Z are not simultaneously $NR^1CH_2CH_2O$ and $O(CH_2)_{n-1}$, respectively. In more particular examples of any of the foregoing, A may represent an optionally substituted cyclohexyl group, in which J is $CHOR^3$ or $CHR^4$. In still more particular examples of any of the foregoing, A may be 4-hydroxycyclohexyl.

In some embodiments, A may represent an optionally substituted cyclohexyl group defined as in Formula 19 and specified above, and X may be $NR^1(1,2$-cyclopentyl), $NR^1(1,3$-cyclopentyl), $NR^1(1,2$-cyclohexyl), $NR^1(1,3$-cyclohexyl), or $NR^1(1,4$-cyclohexyl). $R^1$ may be H or $C_1-C_6$ alkyl, and Z and $R^2$ may be defined as above. $R^1$ may be H any examples of such mitofusin activators. In more particular examples of such mitofusin activators, Z may be $(CH_2)_n$ or $O(CH_2)_{n-1}$, wherein n is an integer ranging from 2 to 4. In more particular examples of any of the foregoing, A may represent an optionally substituted cyclohexyl group, in which J is $CHOR^3$ or $CHR^4$. In still more particular examples of any of the foregoing, A may be 4-hydroxycyclohexyl.

In more specific examples, the mitofusin activators disclosed herein may have structures represented by Formulas 20-25 below.

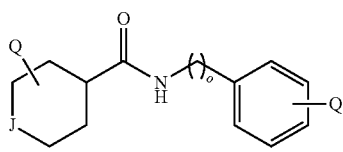

Formula 20

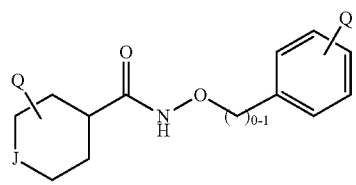

Formula 21

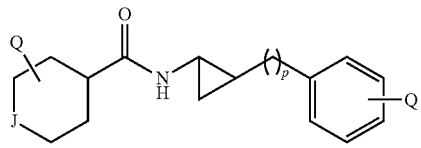

Formula 22

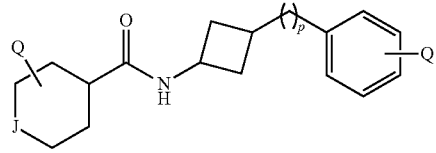

Formula 23

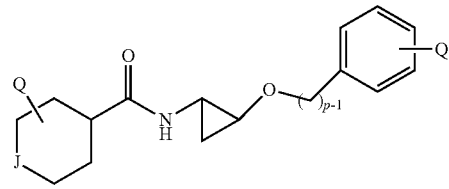

Formula 24

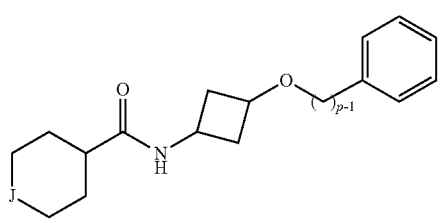

Formula 25

In Formulas 20 and 21, o is an integer ranging from 4 to 6, and in Formulas 22-25, p is an integer ranging from 2 to 4.

In still more specific examples, the mitofusin activators may have structures represented by Formulas 26 to 34 below or any stereoisomer thereof.

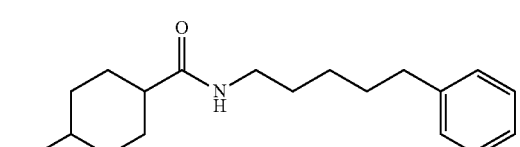

Formula 26

4-hydroxy-N-(5-phenylpentyl)cyclohexane-1-carboxamide

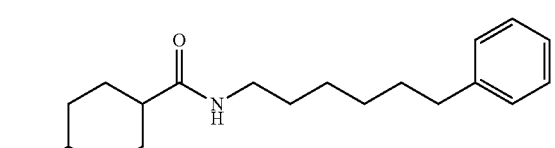

Formula 27

4-hydroxy-N-(6-phenylhexyl)cyclohexane-1-carboxamide

Formula 28

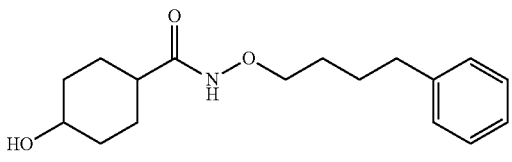

4-hydroxy-N-(4-phenylbutoxy)cyclohexane-1-carboxamide

Formula 29

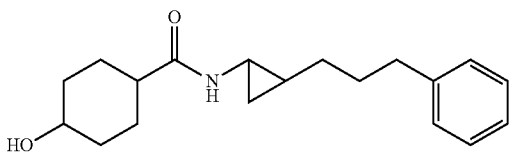

4-hydroxy-N-(2-(3-phenylpropyl)cyclopropyl)cyclohexane-1-carboxamide

Formula 30

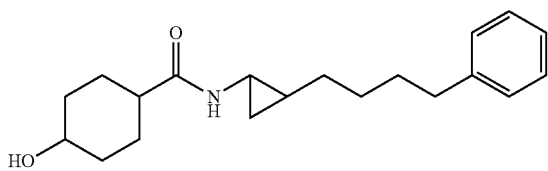

4-hydroxy-N-(2-(4-phenylbutyl)cyclopropyl)cyclohexane-1-carboxamide

Formula 31

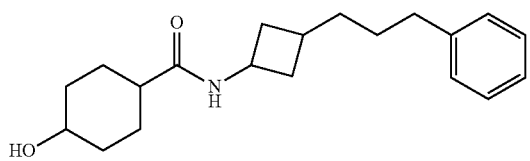

4-hydroxy-N-(3-(3-phenylpropyl)cyclobutyl)cyclohexane-1-carboxamide

Formula 32

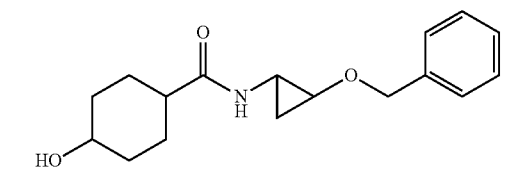

N-(2-(benzyloxy)cyclopropyl)-4-hydroxycyclohexane-1-carboxamide

Formula 33

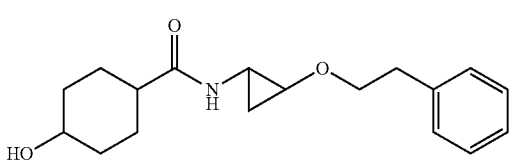

4-hydroxy-N-(2-phenethoxycyclopropyl)cyclohexane-1-carboxamide

Formula 34

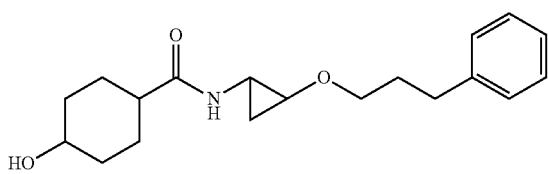

4-hydroxy-N-(2-(3-phenylpropoxy)cyclopropyl)cyclohexane-1-carboxamide

Any of the foregoing mitofusion activators may be present as a mixture of stereoisomers (enantiomers or diastereomers, depending on structure), or a single enantiomer or diastereomer may be present. Suitable techniques for resolving stereoisomers of the mitofusin activators or synthetic techniques for producing a particular stereoisomer of the mitofusin activators will be familiar to one having ordinary skill in the art. In a non-limiting example, any mitofusin activator having variable A as a 4-hydroxypiperidine group may contain the R-enantiomer of the 4-hydroxypiperidine group.

As used herein, the term "pharmaceutically acceptable salt" refers to organic or inorganic salts of a compound of the present disclosure that have specified toxicity and/or biodistribution properties. Suitable salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and/or pamoate (i.e., 1,1'-methylene-bis-(2-hydroxy-3-naphthoate)) salts. The pharmaceutically acceptable salt may balance charge on the parent compound by being present as a counterion. More than one counterion may be present. When multiple counterions are present, the compounds may be present as a mixed pharmaceutically acceptable salt.

Pharmaceutically acceptable salts and/or hydrates of the mitofusin activators may also be present in the compositions of the present disclosure. As used herein, the term "pharmaceutically acceptable solvate" refers to an association between one or more solvent molecules and a mitofusin activator of the present disclosure or a salt thereof, wherein the solvate has specified toxicity and/or biodistribution properties. Examples of solvents that may form pharmaceutically acceptable solvates include, but are not limited to, water, isopropanol, ethanol, methanol, DMSO, ethyl acetate, acetic acid, and/or ethanolamine. As used herein, the term "pharmaceutically acceptable hydrate" refers to a mitofusin activator of the present disclosure or a salt thereof that further includes a stoichiometric or non-stoichiometric amount of water bound by non-covalent intermolecular forces, wherein the hydrate has specified toxicity and/or biodistribution properties.

The mitofusin activators described herein may be formulated using one or more pharmaceutically acceptable excipients (carriers) known to persons having ordinary skill in the art. The term "pharmaceutically acceptable excipient," as used herein, refers to substances or components that do not cause unacceptable losses of pharmacological activity or unacceptable adverse side effects when administered to a subject. Example "pharmaceutically acceptable excipients" include, but are not limited to, solvents, dispersion media, coatings, antibacterial agents, antifungal agents, isotonic, and absorption delaying agents, provided that any of these agents do not produce significant side effects or are incompatible with the mitofusin activator in the composition. Example excipients are described, for example, in Remington's Pharmaceutical Sciences (A. R. Gennaro, Ed.), 21st edition, ISBN: 0781746736 (2005) and United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF may also be used. Such formulations may contain a therapeutically effective amount of one or more mitofusin activators, optionally as a salt, hydrate, and/or solvate, together with a suitable amount of excipient to provide a form for proper administration to a subject.

Compositions of the present disclosure may be stable to specified storage conditions. A "stable" composition refers to a composition having sufficient stability to allow storage at a convenient temperature, such as from about 0° C. to about 60° C. or about −20° C. to about 50° C., for a commercially reasonable period of time, such as at least about one day, at least about one week, at least about one month, at least about three months, at least about six months, at least about one year, or at least about two years.

Compositions of the present disclosure may be tailored to suit a desired mode of administration, which may include, but are not limited to, parenteral, pulmonary, oral, topical, transdermal, intradermal, intramuscular, intraperitoneal, intravenous, subcutaneous, intranasal, epidural, ophthalmic, pulmonary, epidural, buccal, vaginal, and rectal. The compositions may also be administered in combination with one or more additional agents or together with other biologically active or biologically inert agents.

Controlled-release (or sustained-release) compositions may be formulated to extend the activity of the mitofusin activators and reduce dosing frequency. Controlled-release compositions may also be used to affect the time of onset of action or other characteristics, such as plasma levels of the mitofusin activator, and consequently affect the occurrence of side effects. Controlled-release compositions may be designed to initially release an amount of one or more mitofusin activators that produces the desired therapeutic effect, and gradually and continually release other amounts of the mitofusin activator to maintain the level of therapeutic effect over an extended period. In order to maintain a near-constant level of mitofusin activator in the body, the mitofusin activator may be released at a rate sufficient to replace the amount being metabolized or excreted from a subject. The controlled-release may be stimulated by various inducers (e.g., change in pH, change in temperature, enzymes, water, or other physiological conditions or molecules).

Agents or compositions described herein may also be used in combination with other therapeutic modalities, as described further below. Thus, in addition to the therapies described herein, one may also provide to the subject other therapies known to be efficacious for treatment of a disease, disorder, or condition being targeted by the mitofusin activator or a related disease, disorder, or condition.

Mitofusin activators of the present disclosure may stimulate mitochondrial fusion, increase mitochondrial fitness, and enhance mitochondrial subcellular transport. Accordingly, in another aspect of the present disclosure, any one or a combination of mitofusin activators of the present disclosure or a pharmaceutically acceptable salt thereof may be administered in a therapeutically effective amount to a subject having or suspected of having a mitochondria-associated disease, disorder or condition. The subject may be a human or other mammal having or suspected of having a mitochondria-associated disease, disorder or condition.

The mitochondria-associated disease, disorder or condition may be a pheripheral nervous system (PNS) or central nervous system (CNS) genetic or non-genetic disorder, physical damage, and/or chemical injury. In some aspects, in the method of treating a disease, disorder or condition for which a mitofusin activator is indicated, the PNS or CNS disorder may be selected from any one or a combination of: a chronic neurodegenerative condition wherein mitochondrial fusion, fitness, or trafficking are impaired; a disease or disorder associated with mitofusin-1 (MFN1) or mitofusin-2 (MFN2) dysfunction; a disease associated with mitochondrial fragmentation, dysfunction, or dysmotility; a degenerative neuromuscular condition such as Charcot-Marie-Tooth disease, amyotrophic lateral sclerosis (ALS), Huntington's disease, Alzheimer's disease, Parkinson's disease, hereditary motor and sensory neuropathy, autism, autosomal dominant optic atrophy (ADOA), muscular dystrophy, Lou Gehrig's disease, cancer, mitochondrial myopathy, diabetes mellitus and deafness (DAD), Leber's hereditary optic neuropathy (LHON), Leigh syndrome, subacute sclerosing encephalopathy, neuropathy, ataxia, retinitis pigmentosa, and ptosis (NARP), myoneurogenic gastrointestinal encephalopathy (MNGIE), myoclonic epilepsy with ragged red fibers (MERRF), mitochondrial myopathy, encephalomyopathy, lactic acidosis, stroke-like symptoms (MELAS), mtDNA depletion, mitochondrial neurogastrointestinal encephalomyopathy (MNGIE), dysautonomic mitochondrial myopathy, mitochondrial channelopathy, or pyruvate dehydrogenase complex deficiency (PDCD/PDH), diabetic neuropathy, chemotherapy-induced peripheral neuropathy, crush injury, SCI, traumatic brain injury (TBI), stroke, optic nerve injury, and/or related conditions that involve axonal disconnection.

Other mitochondria-associated diseases, disorders, or conditions that may be treated with the compositions disclosed herein, but are not limited to, Alzheimer's disease, ALS, Alexander disease, Alpers' disease, Alpers-Huttenlocher syndrome, alpha-methylacyl-CoA racemase deficiency, Andermann syndrome, Arts syndrome, ataxia neuropathy spectrum, ataxia (e.g., with oculomotor apraxia, autosomal dominant cerebellar ataxia, deafness, and narcolepsy), autosomal recessive spastic ataxia of Charlevoix-Saguenay, Batten disease, beta-propeller protein-associated neurodegeneration, cerebro-oculo-facio-skeletal syndrome (COFS), corticobasal degeneration, CLN1 disease, CLN10 disease, CLN2 disease, CLN3 disease, CLN4 disease, CLN6 disease, CLN7 disease, CLN8 disease, cognitive dysfunction, congenital insensitivity to pain with anhidrosis, dementia, familial encephalopathy with neuroserpin inclusion bodies, familial British dementia, familial Danish dementia, fatty acid hydroxylase-associated neurodegeneration, Friedreich's Ataxia, Gerstmann-Straussler-Scheinker Disease, GM2-gangliosidosis (e.g., AB variant), HMSN type 7 (e.g., with retinitis pigmentosa), Huntington's disease, infantile neuroaxonal dystrophy, infantile-onset ascending hereditary spastic paralysis, infantile-onset spinocerebellar ataxia, juvenile primary lateral sclerosis, Kennedy's disease, Kuru, Leigh's Disease, Marinesco-Sjögren syndrome, mild cognitive impairment (MCI), mitochondrial membrane protein-associated neurodegeneration, motor neuron disease, monomelic amyotrophy, motor neuron diseases (MND), multiple system atrophy, multiple system atrophy with orthostatic hypotension (Shy-Drager Syndrome), multiple sclerosis, multiple system atrophy, neurodegeneration in down's syndrome (NDS), neurodegeneration of aging, neurodegeneration with brain iron accumulation, neuromyelitis optica, pantothenate kinase-associated neurodegeneration, opsoclonus myoclonus, prion disease, progressive multifocal leukoencephalopathy, Parkinson's disease, Parkinson's disease-related disorders, polycystic lipomembranous osteodysplasia with sclerosing leukoencephalopathy, prion disease, progressive external ophthalmoplegia, riboflavin transporter deficiency neuronopathy, Sandhoff disease, spinal muscular atrophy (SMA), spinocerebellar ataxia (SCA), striatonigral degeneration, transmissible spongiform encephalopathies (prion diseases), and/or Wallerian-like degeneration.

Still other mitochrondria-associated diseases, disorders, or conditions that may be treated with the compositions disclosed herein include abulia; agraphia; alcoholism; alexia; alien hand syndrome; Allan-Herndon-Dudley syndrome; alternating hemiplegia of childhood; Alzheimer's disease; amaurosis fugax; amnesia; ALS; aneurysm; angelman syndrome; anosognosia; aphasia; apraxia; arachnoiditis; Arnold-Chiari malformation; asomatognosia; Asperger syndrome; ataxia; attention deficit hyperactivity disorder; atr-16 syndrome; auditory processing disorder; autism spectrum; Behcets disease; bipolar disorder; Bell's palsy; brachial plexus injury; brain damage; brain injury; brain tumor; Brody myopathy; Canavan disease; capgras delusion; carpal tunnel syndrome; causalgia; central pain syndrome; central pontine myelinolysis; centronuclear myopathy; cephalic disorder; cerebral aneurysm; cerebral arteriosclerosis; cerebral atrophy; cerebral autosomal dominant arteriopathy with subcortical infarcts and leukoencephalopathy (CADASIL); cerebral dysgenesis-neuropathy-ichthyosis-keratoderma syndrome (CEDNIK syndrome); cerebral gigantism; cerebral palsy; cerebral vasculitis; cervical spinal stenosis; Charcot-Marie-Tooth disease; chiari malformation; chorea; chronic fatigue syndrome; chronic inflammatory demyelinating polyneuropathy (CIDP); chronic pain; Cockayne syndrome; Coffin-Lowry syndrome; coma; complex regional pain syndrome; compression neuropathy; congenital facial diplegia; corticobasal degeneration; cranial arteritis; craniosynostosis; Creutzfeldt-Jakob disease; cumulative trauma disorders; Cushing's syndrome; cyclothymic disorder; cyclic vomiting syndrome (CVS); cytomegalic inclusion body disease (CIBD); cytomegalovirus infection; Dandy-Walker syndrome; dawson disease; de Morsier's syndrome; Dejerine-Klumpke palsy; Dejerine-Sottas disease; delayed sleep phase syndrome; dementia; dermatomyositis; developmental coordination disorder; diabetic neuropathy; diffuse sclerosis; diplopia; disorders of consciousness; down syndrome; Dravet syndrome; duchenne muscular dystrophy; dysarthria; dysautonomia; dyscalculia; dysgraphia; dyskinesia; dyslexia; dystonia; empty sella syndrome; encephalitis; encephalocele; encephalotrigeminal angiomatosis; encopresis; enuresis; epilepsy; epilepsy-intellectual disability in females; erb's palsy; erythromelalgia; essential tremor; exploding head syndrome; Fabry's disease; Fahr's syndrome; fainting; familial spastic paralysis; febrile seizures; Fisher syndrome; Friedreich's ataxia; fibromyalgia; Foville's syndrome; fetal alcohol syndrome; fragile x syndrome; fragile x-associated tremor/ataxia syndrome (FX-TAS); Gaucher's disease; generalized epilepsy with febrile seizures plus; Gerstmann's syndrome; giant cell arteritis; giant cell inclusion disease; globoid cell leukodystrophy; gray matter heterotopia; Guillain-Barré syndrome; generalized anxiety disorder; HTLV-1 associated myelopathy; Hallervorden-Spatz syndrome; head injury; headache; hemifacial spasm; hereditary spastic paraplegia; heredopathia atactica polyneuritiformis; herpes zoster oticus; herpes zoster; Hirayama syndrome; Hirschsprung's disease; Holmes-Adie syndrome; holoprosencephaly; Huntington's disease; hydranencephaly; hydrocephalus; hypercortisolism; hypoxia; immune-mediated encephalomyelitis; inclusion body myositis; incontinentia pigmenti; infantile refsum disease; infantile spasms; inflammatory myopathy; intracranial cyst; intracranial hypertension; isodicentric 15; Joubert syndrome; Karak syndrome; Kearns-Sayre syndrome; Kinsbourne syndrome; Kleine-Levin syndrome; Klippel Feil syndrome; Krabbe disease; Kufor-Rakeb syndrome; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; leukoencephalopathy with vanishing white matter; lewy body dementia; lissencephaly; locked-in syndrome; Lou Gehrig's disease (amyotrophic lateral sclerosis (ALS)); lumbar disc disease; lumbar spinal stenosis; lyme disease-neurological sequelae; Machado-Joseph disease (spinocerebellar ataxia type 3); macrencephaly; macropsia; mal de debarquement; megalencephalic leukoencephalopathy with subcortical cysts; megalencephaly; Melkersson-Rosenthal syndrome; menieres disease; meningitis; Menkes disease; metachromatic leukodystrophy; microcephaly; micropsia; migraine; Miller Fisher syndrome; mini-stroke (transient ischemic attack); misophonia; mitochondrial myopathy; mobius syndrome; monomelic amyotrophy; Morvan syndrome; motor neurone disease—see ALS; motor skills disorder; moyamoya disease; mucopolysaccharidoses; multi-infarct dementia; multifocal motor neuropathy; multiple sclerosis; multiple system atrophy; muscular dystrophy; myalgic encephalomyelitis; myasthenia gravis; myelinoclastic diffuse sclerosis; myoclonic encephalopathy of infants; myoclonus; myopathy; myotubular myopathy; myotonia congenita; narcolepsy; neuro-Behçet's disease; neurofibromatosis; neuroleptic malignant syndrome; neurological manifestations of aids; neurological sequelae of lupus; neuromyotonia; neuronal ceroid lipofuscinosis; neuronal migration disorders; neuropathy; neurosis; Niemann-Pick disease; non-24-hour sleep-wake disorder; nonverbal learning disorder; O'Sullivan-McLeod syndrome; occipital neuralgia; occult spinal dysraphism sequence; Ohtahara syndrome; olivopontocerebellar atrophy; opsoclonus myoclonus syndrome; optic neuritis; orthostatic hypotension; otosclerosis; overuse syndrome; palinopsia; paresthesia; Parkinson's disease; paramyotonia congenita; paraneoplastic diseases; paroxysmal attacks; Parry-Romberg syndrome; pediatric autoimmune neuropsychiatric disorders associated with streptococcoal infections (PANDAS); Pelizaeus-Merzbacher disease; periodic paralyses; peripheral neuropathy; pervasive developmental disorders; phantom limb/phantom pain; photic sneeze reflex; phytanic acid storage disease; Pick's disease; pinched nerve; pituitary tumors; pmg; polyneuropathy; polio; polymicrogyria; polymyositis; porencephaly; post-polio syndrome; postherpetic neuralgia (phn); postural hypotension; Prader-Willi syndrome; primary lateral sclerosis; prion diseases; progressive hemifacial atrophy; progressive multifocal leukoencephalopathy; progressive supranuclear palsy; prosopagnosia; pseudotumor cerebri; quadrantanopia; quadriplegia; rabies; radiculopathy; Ramsay Hunt syndrome type 1; Ramsay Hunt syndrome type 2; Ramsay Hunt syndrome type 3—see Ramsay-Hunt syndrome; Rasmussen encephalitis; reflex neurovascular dystrophy; refsum disease; REM sleep behavior disorder; repetitive stress injury; restless legs syndrome; retrovirus-associated myelopathy; Rett syndrome; Reye's syndrome; rhythmic movement disorder; Romberg syndrome; Saint Vitus' dance; Sandhoff disease; Schilder's disease (two distinct conditions); schizencephaly; sensory processing disorder; septo-optic dysplasia; shaken baby syndrome; shingles; Shy-Drager syndrome; Sjögren's syndrome; sleep apnea; sleeping sickness; snatiation; Sotos syndrome; spasticity; spina bifida; spinal cord injury; spinal cord tumors; spinal muscular atrophy; spinal and bulbar muscular atrophy; spinocerebellar ataxia; split-brain; Steele-Richardson-Olszewski syndrome; stiff-person syndrome; stroke; Sturge- Weber syndrome; stuttering; subacute sclerosing panencephalitis; subcortical arteriosclerotic encephalopathy; superficial siderosis; Sydenham's chorea; syncope; synesthesia; syringomyelia; tarsal tunnel syndrome; tardive dyskinesia; tardive dysphrenia; Tarlov cyst; Tay-Sachs disease; temporal arteritis; temporal lobe epilepsy; tetanus; tethered spinal cord syndrome; Thomsen disease; thoracic outlet syndrome; tic douloureux; Todd's Paralysis; tourette syndrome; toxic encephalopathy; transient ischemic attack; transmissible spongiform encephalopathies; transverse myelitis; traumatic brain injury; tremor; trichotillomania; trigeminal neuralgia; tropical spastic paraparesis; trypanosomiasis; tuberous sclerosis; 22q13 deletion syndrome; Unverricht-Lundborg disease; vestibular schwannoma (acoustic neuroma); Von Hippel-Lindau disease (VHL); viliuisk encephalomyelitis (VE); Wallenberg's syndrome; west syndrome; whiplash; Williams syndrome; Wilson's disease; y-linked hearing impairment; and/or Zellweger syndrome.

Each of the states, diseases, disorders, and conditions, described herein, as well as others, may benefit from compositions and methods described herein. Generally, treating a state, disease, disorder, or condition includes preventing or delaying the appearance of clinical symptoms in a mammal that may be afflicted with or predisposed to the state, disease, disorder, or condition but does not yet experience or display clinical or subclinical symptoms thereof. Treating can also include inhibiting the state, disease, disorder, or condition (e.g., arresting or reducing the development of the disease or at least one clinical or subclinical symptom thereof). Furthermore, treating can include relieving the disease (e.g., causing regression of the state, disease, disorder, or condition or at least one of its clinical or subclinical symptoms). A benefit to a subject to be treated can be either statistically significant or at least perceptible to the subject or to a physician.

A mitochondria-associated disease, disorder, or condition may be a disease primarily caused by or secondarily associated with mitochondrial dysfunction, fragmentation, or loss-of-fusion, or associated with dysfunction in MFN1 or MFN2 catalytic activity or conformational unfolding. Mitochondrial dysfunction may be caused by genetic mutations of mitofusins or other (nuclear or mitochondrial encoded) genes, or may be caused by physical, chemical, or environmental injury to the CNS or PNS.

In a particular example, cancer chemotherapy-induced sensory and motor neuropathies may be prevented or treated with the compositions of the present disclosure. Chemotherapy-induced peripheral neuropathy is one of the most common complications of cancer chemotherapy, affecting 20% of all patients and almost 100% of patients receiving high doses of chemotherapeutic agents. Dose-dependent neurotoxicity of motor and sensory neurons can lead to chronic pain, hypersensitivity to hot, cold, and mechanical stimuli, and/or impaired neuromuscular control. The most common chemotherapeutic agents linked to CIPN are platinum, vinca alkaloids, taxanes, epothilones, and the targeted proteasome inhibitor, bortezomib.

CIPN most commonly affects peripheral sensory neurons whose cell bodies are located in dorsal root ganglia lacking the blood-brain barrier that protects other components of the central and peripheral nervous system. Unprotected dorsal root ganglion neurons are more sensitive to neuronal hyperexcitability and innate immune system activation evoked by circulating cytotoxic chemotherapeutic agents. CIPN affects quality of life, and is potentially disabling, because it provokes chronic neuropathic pain that, like other causes of neuralgia (e.g., post herpetic neuralgia, diabetic mononeuropathy), is refractory to analgesic therapy. Motor nerve involvement commonly manifests as loss of fine motor function with deterioration in hand writing, difficulty in buttoning clothes or sewing, and sometimes upper and lower extremity weakness or loss of endurance. CIPN typically manifests within weeks of chemotherapy and in many cases improves after chemotherapy treatment ends, although residual pain, sensory, or motor defects are observed in one-third to one-half of affected patients. Unfortunately, CIPN-limited chemotherapy dosing can lead to delays, reduction, or interruption of cancer treatment, thus shortening survival.

Mitochondrial dysfunction and oxidative stress are implicated in CIPN because of observed ultrastructural morphological abnormalities, impaired mitochondria DNA transcription and replication, induction of mitochondrial apoptosis pathways, and reduction of experimental CIPN signs by anticipatory mitochondrial protection. Mitofusin activators may enhance overall mitochondrial function in damaged neurons, increase mitochondrial transport to areas of neuronal damage, and accelerate in vitro neuron repair/regeneration after chemotherapy-induced damage. For this reason, it is believed that mitofusin activators may reduce neuronal injury conferred by chemotherapeutic agents in CIPN and accelerate regeneration/repair of nerves damaged by chemotherapeutic anticancer agents. As such, the present disclosure provides for compositions and methods to treat cancer chemotherapy induced nerve injury and neuropathy.

In another example, injury in the CNS or PNS (e.g., trauma to the CNS or PNS, crush injury, SCI, TBI, stroke, optic nerve injury, or related conditions that involve axonal disconnection) may be treated with the compositions of the present disclosure. The CNS includes the brain and the spinal cord and the PNS is composed of cranial, spinal, and autonomic nerves that connect to the CNS.

Damage to the nervous system caused by mechanical, thermal, chemical, or ischemic factors may impair various nervous system functions such as memory, cognition, language, and voluntary movement. Most often, this is through accidental crush or transection of nerve tracts, or as an unintended consequence of medical interventions, that interrupt normal communications between nerve cell bodies and their targets. Other types of injuries may include disruption of the interrelations between neurons and their supporting cells or the destruction of the blood-brain barrier.

Mitofusin activators may rapidly reverse mitochondrial dysmotility in neurons from mice or patients with various genetic or chemotherapeutic neurodegenerative diseases, in axons injured by chemotherapeutic agents, and in axons severed by physical injury. For this reason, mitofusin activators may enhance regeneration/repair of physically damaged nerves, as in vehicular and sports injuries, penetration trauma from military or criminal actions, and iatrogenic injury during invasive medical procedures. As such, the present disclosure provides for compositions and methods to treat physical nerve injury.

Mitochondrial motility is also implicated in neuropathy and traumatic crush or severance nerve injuries. After nerve laceration or crush injury, nerves will either regenerate and restore neuromuscular function or fail to regenerate such that neuromuscular function in permanently impaired. Mitofusin activators may increase mitochondrial trafficking, thereby enabling a nerve to regenerate after traumatic injuries.

The amount of a mitofusin activator and excipient to produce a composition in a given dosage form may vary depending upon the subject being treated, the condition being treated and the particular mode of administration. It will be appreciated that the unit content of mitofusin activator contained in an individual dose of a given dosage form need not in itself constitute a therapeutically effective amount, as the necessary therapeutically effective amount could be reached by administration of a number of individual doses, or the therapeutic effect may be cumulative over time.

Dosing of the mitofusin activators of the present disclosure may occur as a single event or over a time course of treatment. For example, a mitofusin activator may be administered daily, weekly, bi-weekly, or monthly. For treatment of acute conditions, the time course of treatment may be at least several days, with dosing taking place at least once a day or continuously. Certain conditions could extend treatment from several days to several weeks. For example, treatment could extend over one week, two weeks, or three weeks. For chronic conditions, treatment could extend from several weeks to several months or even years.

Toxicity and therapeutic efficacy of the compositions described herein may be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that may be expressed as the ratio $LD_{50}/ED_{50}$, where larger therapeutic indices are generally understood in the art to be optimal.

Embodiments disclosed herein include:

A. Compositions comprising a mitofusin activator. The mitofusin activator has a structure represented by

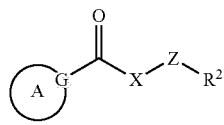

any stereoisomer thereof, or any pharmaceutically acceptable salt thereof; wherein: G is N or CH, and A is an optionally substituted 5- or 6-membered cycloalkyl or heterocycloalkyl ring; X is $(CH_2)_3$, $OCH_2CH_2$, $CH_2OCH_2$, $CH_2CH_2O$, Cyc, $CH_2Cyc$, $NR^1(CH_2)_3$, $NR^1OCH_2CH_2$, $NR^1CH_2OCH_2$, $NR^1CH_2CH_2O$, or $NR^1Cyc$; wherein $R^1$ is H or $C_1$-$C_6$ alkyl, and Cyc is 1,2-cyclopropyl, 1,2-cyclobutyl, 1,3-cyclobutyl, 1,2-cyclopentyl, 1,3-cyclopentyl, 1,2-cyclohexyl, 1,3-cyclohexyl, or 1,4-cyclohexyl; Z is $(CH_2)_n$ or $(CH_2)_{n_1}O(CH_2)_{n_2}$; wherein n is an integer ranging from 1 to 5, n1 is an integer ranging from 0 to 4, n2 is an integer ranging from 0 to 4, and $n_1+n_2=n-1$; and $R^2$ is an optionally substituted aryl or heteroaryl group.

B. Methods for administering a mitofusin activator to a subject having or suspected of having a mitochondria-associated disease. The methods comprise: administering a therapeutically effective amount of the composition of A, any stereoisomer thereof, or any pharmaceutically acceptable salt thereof to a subject having or suspected of having a mitochondria-associated disease, disorder, or condition.

Embodiments A and B may have one or more of the following additional elements in any combination.

Element 1: wherein $R^2$ is an optionally substituted phenyl group.

Element 2: wherein G is N and A represents an optionally substituted piperidinyl, piperazinyl, morpholinyl, or pyrrolidinyl group.

Element 3: wherein the mitofusin activator has a structure represented by

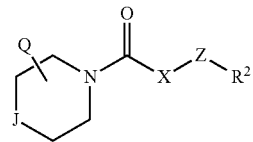

or any stereoisomer thereof; wherein J is a bond, CH(hal), $CHOR^3$, $CHR^4$, $CHNR^4R^5$, O, or $NR^4$, and Q is an optional substitution; wherein hal is a halogen, $R^3$ is H or $C_1$-$C_6$ alkyl, and $R^4$ and $R^5$ are independently H, $C_1$-$C_6$ alkyl, or $C_1$-$C_6$ acyl.

Element 4: wherein J is $CHOR^3$ or $CHR^4$.

Element 5: wherein X is $(CH_2)_3$, 1,2-cyclopropyl, 1,2-cyclobutyl, or 1,3-cyclobutyl.

Element 6: wherein Z is $(CH_2)_n$ or $O(CH_2)_{n-1}$, and n is an integer ranging from 2 to 5.

Element 7: wherein A is 4-hydroxypiperidinyl.

Element 8: wherein the mitofusin activator has a structure represented by

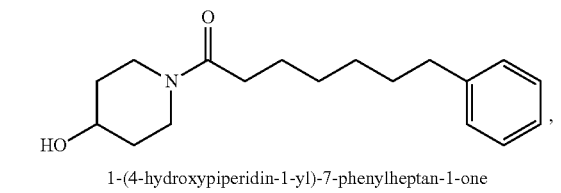

1-(4-hydroxypiperidin-1-yl)-7-phenylheptan-1-one

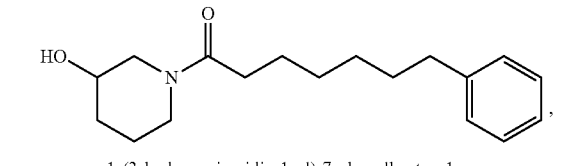

1-(3-hydroxypiperidin-1-yl)-7-phenylheptan-1-one

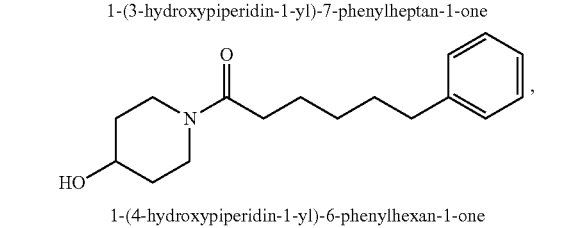

1-(4-hydroxypiperidin-1-yl)-6-phenylhexan-1-one

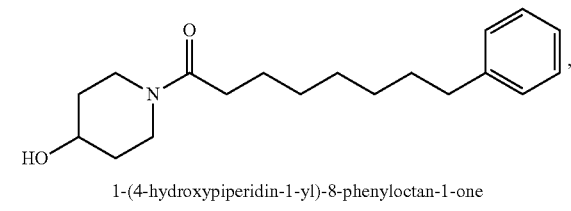

1-(4-hydroxypiperidin-1-yl)-8-phenyloctan-1-one

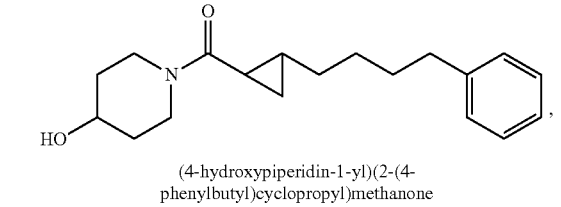

(4-hydroxypiperidin-1-yl)(2-(4-phenylbutyl)cyclopropyl)methanone

-continued

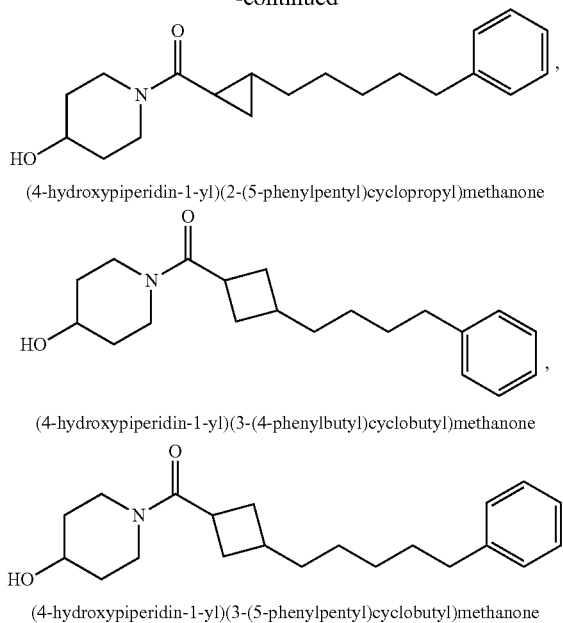

(4-hydroxypiperidin-1-yl)(2-(5-phenylpentyl)cyclopropyl)methanone (4-hydroxypiperidin-1-yl)(3-(4-phenylbutyl)cyclobutyl)methanone (4-hydroxypiperidin-1-yl)(3-(5-phenylpentyl)cyclobutyl)methanone or any stereoisomer thereof.

Element 9: wherein X is $NR^1(CH_2)_3$, $NR^1(1,2$-cyclopropyl), $NR^1(1,2$-cyclobutyl), or $NR^1(1,3$-cyclobutyl).

Element 10: wherein Z is $(CH_2)_n$ or $O(CH_2)_{n-1}$, and n is an integer ranging from 1 to 4.

Element 11: wherein the mitofusin activator has a structure represented by

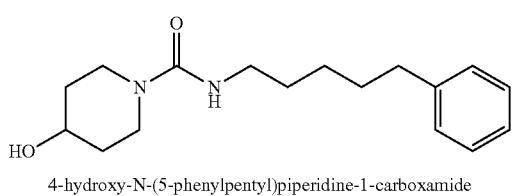 [SMILES: O=C(NCCCCCc1ccccc1)N1CCC(O)CC1]

4-hydroxy-N-(5-phenylpentyl)piperidine-1-carboxamide stereoisomer thereof.

Element 12: wherein G is CH and A represents an optionally substituted piperidinyl, pyrrolidinyl, tetrahydropyranyl, tetrahydrofuranyl, cyclopentyl, or cyclohexyl group.

Element 13: wherein the mitofusin activator has a structure represented by

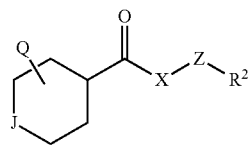

or any stereoisomer thereof; wherein J is a bond, CH(hal), $CHOR^3$, $CHR^4$, $CHNR^4R^5$, O, or $NR^4$, and Q is an optional substitution; wherein hal is a halogen, $R^3$ is H or $C_1$-$C_6$ alkyl, and $R^4$ and $R^5$ are independently H, $C_1$-$C_6$ alkyl, or $C_1$-$C_6$ acyl.

Element 14: wherein Z is $(CH_2)_n$ or $O(CH_2)_{n-1}$, and n is an integer ranging from 2 to 4.

Element 15: wherein A is 4-hydroxycyclohexyl.

Element 16: wherein the mitofusin activator has a structure represented by

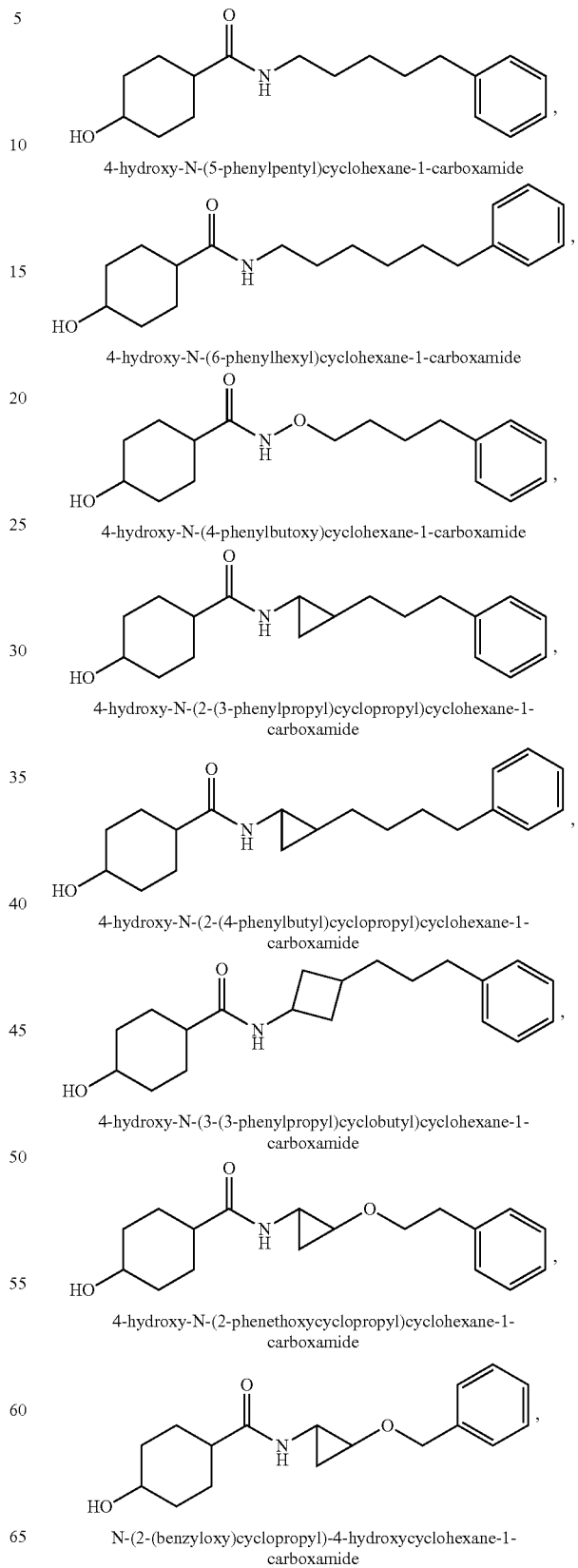

4-hydroxy-N-(5-phenylpentyl)cyclohexane-1-carboxamide 4-hydroxy-N-(6-phenylhexyl)cyclohexane-1-carboxamide 4-hydroxy-N-(4-phenylbutoxy)cyclohexane-1-carboxamide 4-hydroxy-N-(2-(3-phenylpropyl)cyclopropyl)cyclohexane-1-carboxamide 4-hydroxy-N-(2-(4-phenylbutyl)cyclopropyl)cyclohexane-1-carboxamide 4-hydroxy-N-(3-(3-phenylpropyl)cyclobutyl)cyclohexane-1-carboxamide 4-hydroxy-N-(2-phenethoxycyclopropyl)cyclohexane-1-carboxamide N-(2-(benzyloxy)cyclopropyl)-4-hydroxycyclohexane-1-carboxamide

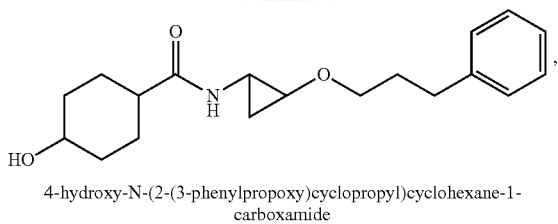

4-hydroxy-N-(2-(3-phenylpropoxy)cyclopropyl)cyclohexane-1-carboxamide or any stereoisomer thereof.

Element 17: wherein the composition further comprises a pharmaceutically acceptable excipient.

Element 18: wherein the mitochondria-associated disease, disorder or condition is a peripheral nervous system (PNS) or central nervous system (CNS) genetic or non-genetic disorder, physical damage, and/or chemical injury.

Element 19: wherein the PNS or CNS disorder is one or more conditions selected from the group consisting of a chronic neurodegenerative condition in which mitochondrial fusion, fitness, and/or trafficking is/are impaired; a disease or disorder associated with mitofusin 1 (MFN1) or mitofusin 2 (MFN2) dysfunction; a disease associated with mitochondrial fragmentation, dysfunction, and/or dysmotility; a degenerative neuromuscular condition; Charcot-Marie-Tooth disease; Amyotrophic Lateral Sclerosis; Huntington's disease; Alzheimer's disease; Parkinson's disease; hereditary motor and sensory neuropathy; autism; autosomal dominant optic atrophy (ADOA); muscular dystrophy; Lou Gehrig's disease; cancer; mitochondrial myopathy; diabetes mellitus and deafness (DAD); Leber's hereditary optic neuropathy (LHON); Leigh syndrome; subacute sclerosing encephalopathy; neuropathy, ataxia, retinitis pigmentosa, and ptosis (NARP); myoneurogenic gastrointestinal encephalopathy (MNGIE); myoclonic epilepsy with ragged red fibers (MERRF); mitochondrial myopathy, encephalomyopathy, lactic acidosis, and stroke-like symptoms (MELAS); mtDNA depletion; mitochondrial neurogastrointestinal encephalomyopathy (MNGIE); dysautonomic mitochondrial myopathy; mitochondrial channelopathy; pyruvate dehydrogenase complex deficiency (PDCD/PDH); diabetic neuropathy; chemotherapy-induced peripheral neuropathy; crush injury; spinal cord injury (SCI); traumatic brain injury; stroke; optic nerve injury; conditions that involve axonal disconnection; and any combination thereof.

By way of non-limiting example, exemplary combinations applicable to A and B include, but are not limited to, 1, and 2 or 3; 1, 3 and 4; 1, and 3-5; 1 and 8; 1, 2 and 9; 1-3 and 9; 1-3, 9 and 10; 1 and 11; 1 and 12; 1, 12 and 13; 1, 9, 12 and 13; 1, 9, and 12-14; 1 and 16; 3 and 4; 3-5; 3 and 5; 3 and 6; 3 and 7; 3 and 9; 3, 4 and 9; 3, 4, 9 and 10; 3 and 7; 12 and 13; 12 and 14; 12-14; 4, 12 and 13; 4 and 12-14; 4, 12 and 15; 12 and 15; 12, 14 and 15; and 4, 12, 14 and 15. Any of the foregoing may be in further combination with 17. Additional exemplary combinations applicable to B include any of the foregoing in further combination with one or more of 17, 18 or 19.

The present disclosure is further directed to the following non-limiting clauses:

Clause 1. A composition comprising:
a mitofusin activator having a structure represented by

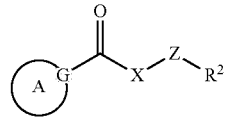

any stereoisomer thereof, or any pharmaceutically acceptable salt thereof;
wherein:
G is N or CH, and A is an optionally substituted 5- or 6-membered cycloalkyl or heterocycloalkyl ring;
X is $(CH_2)_3$, $OCH_2CH_2$, $CH_2OCH_2$, $CH_2CH_2O$, Cyc, $CH_2Cyc$, $NR^1(CH_2)_3$, $NR^1OCH_2CH_2$, $NR^1CH_2OCH_2$, $NR^1CH_2CH_2O$, or $NR^1Cyc$;
wherein $R^1$ is H or $C_1$-$C_6$ alkyl, and Cyc is 1,2-cyclopropyl, 1,2-cyclobutyl, 1,3-cyclobutyl, 1,2-cyclopentyl, 1,3-cyclopentyl, 1,2-cyclohexyl, 1,3-cyclohexyl, or 1,4-cyclohexyl;
Z is $(CH_2)_n$ or $(CH_2)_{n_1}O(CH_2)_{n_2}$;
wherein n is an integer ranging from 1 to 5, n1 is an integer ranging from 0 to 4, n2 is an integer ranging from 0 to 4, and $n_1+n_2=n-1$; and
$R^2$ is an optionally substituted aryl or heteroaryl group.

Clause 2. The composition of clause 1, wherein $R^2$ is an optionally substituted phenyl group.

Clause 3. The composition of clause 1 or clause 2 (or the composition of clause 1), wherein G is N and A represents an optionally substituted piperidinyl, piperazinyl, morpholinyl, or pyrrolidinyl group.

Clause 4. The composition of clause 3, wherein the mitofusin activator has a structure represented by

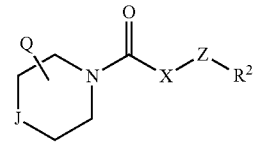

or any stereoisomer thereof;
wherein J is a bond, CH(hal), $CHOR^3$, $CHR^4$, $CHNR^4R^5$, O, or $NR^4$, and Q is an optional substitution;
wherein hal is a halogen, $R^3$ is H or $C_1$-$C_6$ alkyl, and $R^4$ and $R^5$ are independently H, $C_1$-$C_6$ alkyl, or $C_1$-$C_6$ acyl.

Clause 5. The composition of clause 4, wherein J is $CHOR^3$ or $CHR^4$.

Clause 6. The composition of any one of clauses 3-5 (or the composition of clause 3), wherein X is $(CH_2)_3$, 1,2-cyclopropyl, 1,2-cyclobutyl, or 1,3-cyclobutyl.

Clause 7. The composition of any one of clauses 3-6 (or the composition of clause 6), wherein Z is $(CH_2)_n$ or $O(CH_2)_{n-1}$, and n is an integer ranging from 2 to 5.

Clause 8. The composition of any one of clauses 3-7 (or the composition of clause 6), wherein A is 4-hydroxypiperidinyl.

Clause 9. The composition of any one of clauses 3-8 (or the composition of clause 6), wherein $R^2$ is optionally substituted phenyl.

Clause 10. The composition of any one of clauses 3-9 (or the composition of clause 3), wherein the mitofusin activator has a structure represented by

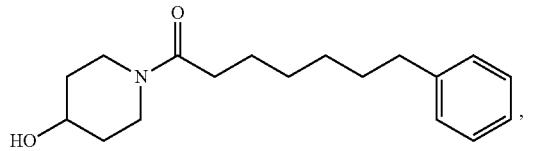

1-(4-hydroxypiperidin-1-yl)-7-phenylheptan-1-one

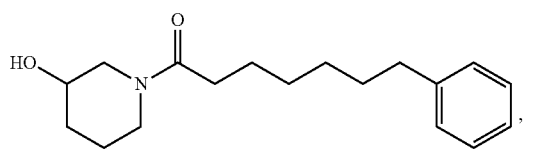

1-(3-hydroxypiperidin-1-yl)-7-phenylheptan-1-one

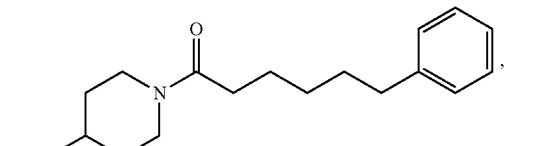

1-(4-hydroxypiperidin-1-yl)-6-phenylhexan-1-one

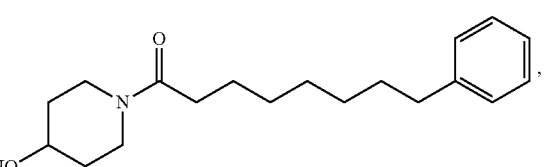

1-(4-hydroxypiperidin-1-yl)-8-phenyloctan-1-one

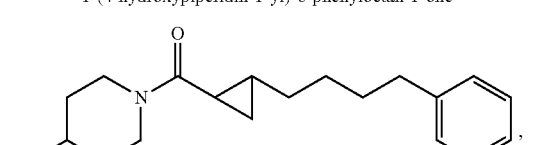

(4-hydroxypiperidin-1-yl)(2-(4-phenylbutyl)cyclopropyl)methanone

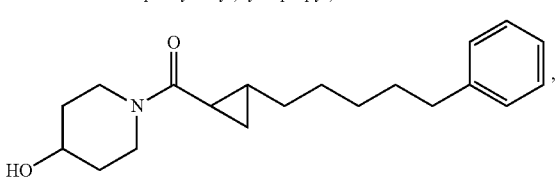

(4-hydroxypiperidin-1-yl)(2-(5-phenylpentyl)cyclopropyl)methanone

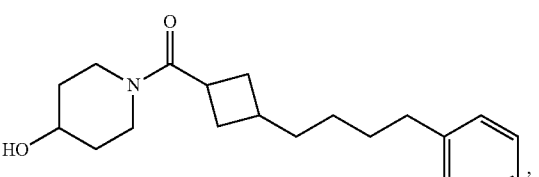

(4-hydroxypiperidin-1-yl)(3-(4-phenylbutyl)cyclobutyl)methanone

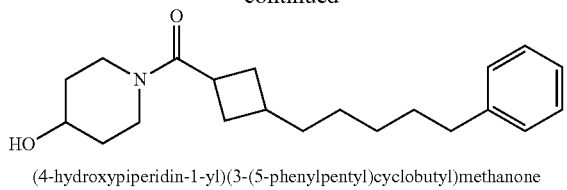

(4-hydroxypiperidin-1-yl)(3-(5-phenylpentyl)cyclobutyl)methanone or any stereoisomer thereof.

Clause 11. The composition of any one of clauses 3-5 (or the composition of clause 3), wherein X is $NR^1(CH_2)_3$, $NR^1(1,2\text{-cyclopropyl})$, $NR^1(1,2\text{-cyclobutyl})$, or $NR^1(1,3\text{-cyclobutyl})$.

Clause 12. The composition of any one of clauses 3-5 or 11 (or the composition of clause 11), wherein Z is $(CH_2)_n$ or $O(CH_2)_{n-1}$, and n is an integer ranging from 1 to 4.

Clause 13. The composition of any one of clauses 3-5, 11 or 12 (or the composition of clause 6 or clause 11), wherein A is 4-hydroxypiperidinyl.

Clause 14. The composition of any one of clauses 3-5, or 11-13 (or the composition of clause 6 or clause 11), wherein $R^2$ is optionally substituted phenyl.

Clause 15. The composition of any one of clauses 3-5, or 11-14 (or the composition of clause 3), wherein the mitofusin activator has a structure represented by

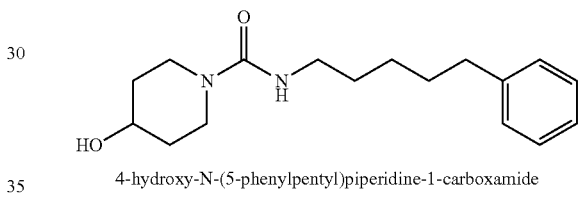

4-hydroxy-N-(5-phenylpentyl)piperidine-1-carboxamide or any stereoisomer thereof.

Clause 16. The composition of clause 1 or clause 2 (or the composition of clause 1), wherein G is CH and A represents an optionally substituted piperidinyl, pyrrolidinyl, tetrahydropyranyl, tetrahydrofuranyl, cyclopentyl, or cyclohexyl group.

Clause 17. The composition of any one of clauses 1, 2, or 16 (or the composition of clause 16), wherein the mitofusin activator has a structure represented by

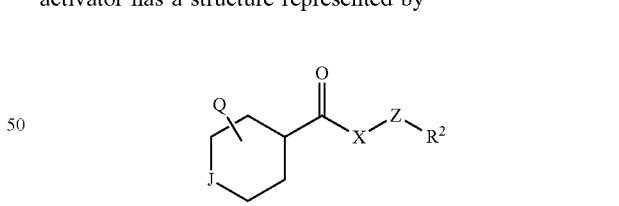

or any stereoisomer thereof;
wherein J is a bond, CH(hal), $CHOR^3$, $CHR^4$, $CHNR^4R^5$, O, or $NR^4$, and Q is an optional substitution;
wherein hal is a halogen, $R^3$ is H or $C_1$-$C_6$ alkyl, and $R^4$ and $R^5$ are independently H, $C_1$-$C_6$ alkyl, or $C_1$-$C_6$ acyl.

Clause 18. The composition of clause 17, wherein J is $CHOR^3$ or $CHR^4$.

Clause 19. The composition of any one of clauses 16-18 (or the composition of clause 17), wherein X is $NR^1(CH_2)_3$, $NR^1(1,2\text{-cyclopropyl})$, $NR^1(1,2\text{-cyclobutyl})$, or $NR^1(1,3\text{-cyclobutyl})$.

Clause 20. The composition of any one of clauses 16-19 (or the composition of clause 19), wherein Z is $(CH_2)_n$ or $O(CH_2)_{n-1}$, and n is an integer ranging from 2 to 4.

Clause 21. The composition of any one of clauses 16-20 (or the composition of clause 19), wherein A is 4-hydroxycyclohexyl.

Clause 22. The composition of any one of clauses 16-21 (or the composition of clause 19), wherein $R^2$ is optionally substituted phenyl.

Clause 23. The composition of any one of clauses 16-22 (or the composition of clause 19), wherein the mitofusin activator has a structure represented by

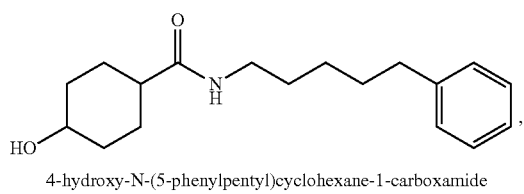

4-hydroxy-N-(5-phenylpentyl)cyclohexane-1-carboxamide

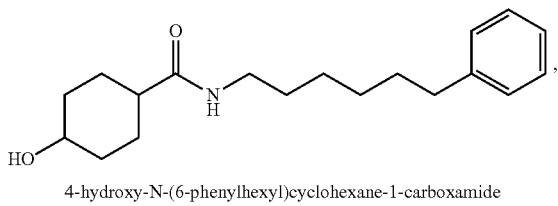

4-hydroxy-N-(6-phenylhexyl)cyclohexane-1-carboxamide

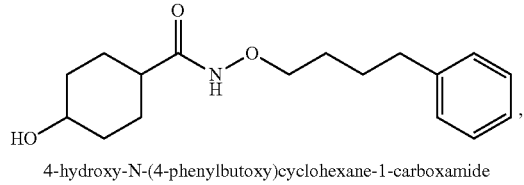

4-hydroxy-N-(4-phenylbutoxy)cyclohexane-1-carboxamide

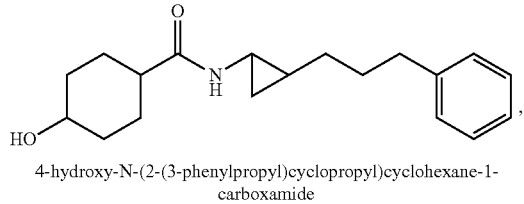

4-hydroxy-N-(2-(3-phenylpropyl)cyclopropyl)cyclohexane-1-carboxamide

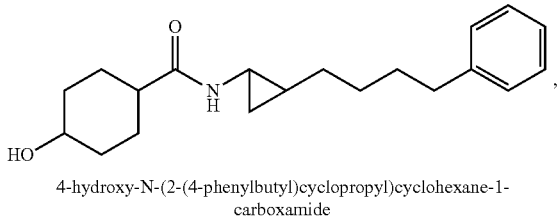

4-hydroxy-N-(2-(4-phenylbutyl)cyclopropyl)cyclohexane-1-carboxamide

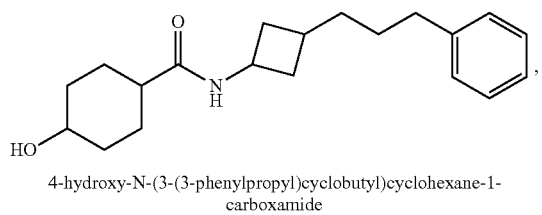

4-hydroxy-N-(3-(3-phenylpropyl)cyclobutyl)cyclohexane-1-carboxamide

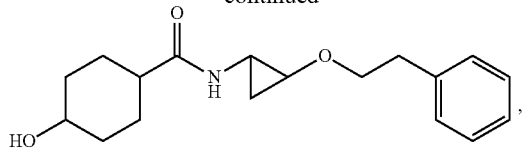

4-hydroxy-N-(2-phenethoxycyclopropyl)cyclohexane-1-carboxamide

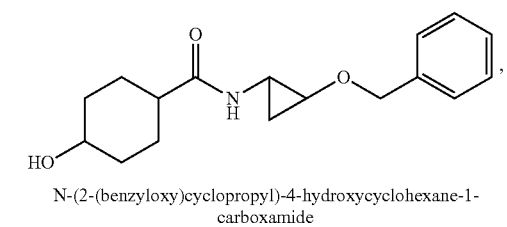

N-(2-(benzyloxy)cyclopropyl)-4-hydroxycyclohexane-1-carboxamide

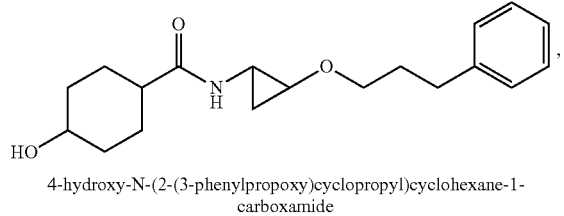

4-hydroxy-N-(2-(3-phenylpropoxy)cyclopropyl)cyclohexane-1-carboxamide or any stereoisomer thereof.

Clause 24. The composition of any one of clauses 1-23 (or the composition of clause 1), further comprising: a pharmaceutically acceptable excipient.

Clause 25. A method comprising:
administering a therapeutically effective amount of the composition of any one of clauses 1-24 (or the composition of any one of clauses 1-5 or 16-18), any stereoisomer thereof, or any pharmaceutically acceptable salt thereof to a subject having or suspected of having a mitochondria-associated disease, disorder, or condition.

Clause 26. The method of clause 25, wherein the mitochondria-associated disease, disorder or condition is a peripheral nervous system (PNS) or central nervous system (CNS) genetic or non-genetic disorder, physical damage, and/or chemical injury.

Clause 27. The method of clause 26, wherein the PNS or CNS disorder is one or more conditions selected from the group consisting of a chronic neurodegenerative condition in which mitochondrial fusion, fitness, and/or trafficking is/are impaired; a disease or disorder associated with mitofusin 1 (MFN1) or mitofusin 2 (MFN2) dysfunction; a disease associated with mitochondrial fragmentation, dysfunction, and/or dysmotility; a degenerative neuromuscular condition; Charcot-Marie-Tooth disease; Amyotrophic Lateral Sclerosis; Huntington's disease; Alzheimer's disease; Parkinson's disease; hereditary motor and sensory neuropathy; autism; autosomal dominant optic atrophy (ADOA); muscular dystrophy; Lou Gehrig's disease; cancer; mitochondrial myopathy; diabetes mellitus and deafness (DAD); Leber's hereditary optic neuropathy (LHON); Leigh syndrome; subacute sclerosing encephalopathy; neuropathy, ataxia, retinitis pigmentosa, and ptosis (NARP); myoneurogenic gastrointestinal encephalopathy (MNGIE); myoclonic epilepsy with ragged red fibers (MERRF); mitochondrial myopathy, encephalomyopathy, lactic acidosis, and stroke-like symptoms (MELAS); mtDNA depletion; mitochondrial neurogastrointestinal encephalomyopathy (MNGIE); dysautonomic mitochondrial myopathy; mitochondrial channelopathy; pyruvate dehydrogenase complex deficiency (PDCD/PDH); diabetic neuropathy; chemotherapy-induced peripheral neuropathy; crush injury; spinal cord injury (SCI); traumatic brain injury; stroke; optic nerve injury; conditions that involve axonal disconnection; and any combination thereof.

To facilitate a better understanding of the present disclosure, the following examples of preferred or representative embodiments are given. In no way should the following examples be read to limit, or to define, the scope of the invention.

EXAMPLES

HPLC analyses were conducted with a Kinetex C18 column (4.6×50 mm, 5 μm; Mobile phase A: 0.0375% TFA in water (v/v), B: 0.01875% TFA in Acetonitrile (v/v)) run at 50° C. with absorbance at 200 nm.

LC-MS/MS (ESI) was performed using 2 systems: 1) SHIMADZU LC-MS-2020 with LABSOLUTION V5.72 analysis software and a CHROMALITH@FLASH RP-18E 25*2.0 mm column run at 50° C. with a PDA (220 and 254 nm) detector, acquired data in scan MS Mode (positive mode) with m/z=100-1000 scan range, drying gas ($N_2$) flow: 15 L/min, DL voltage: 120V and Quarry DC voltage: 20V, or 2) Agilent 1200/G6110A instrument with AgilentChemStation Rev. B. 04.03 software and an XBRIDGE C18 2.1*50 mm column run at 40° C. with DAD (220 nm)/ELSD detector, acquired data in scan MS Mode (positive mode) with m/z=100-1000 scan range, drying gas ($N_2$) flow: 10 L/min, 350° C., nebulizer pressure: 35 psi, capillary voltage: 2500V. NMR spectrometry was carried out on Brucker AVANCE NEO 400 MHz with a 5 mm PABBO BB/19F-1H/D Z-GRD probe.

Dose-response of mitofusin agonist fusogenicity was performed in Mfn1- or Mfn2-deficient MEFs (Mfn1-KO or Mfn2-KO MEFs) cultured at 37° C. and 5% $CO_2$-95% air. Cells were seeded on day 1 in 6 well plates at a density of $2\times10^4$ cells per well and compounds added at 9 concentrations (0.5 nM-10 μM dissolved in DMSO) overnight. Mitochondria were then stained with MitoTracker Orange (200 nM; M7510; Invitrogen, Carlsbad, CA, USA). Nuclei were stained with Hoescht (10 μg/ml; Invitrogen, Thermo Fisher Scientific Cat: #H3570). Images were acquired at room temperature on a Nikon Ti Confocal microscope using a 60×1.3 NA oil-immersion objective in Krebs-Henseleit buffer (138 NaCl, 3.7 nM KCl, 1.2 nM $KH_2PO_4$, 15 nM Glucose, 20 nM HEPES pH: 7.2-7.5, and 1 mM $CaCl_2$). Laser excitation was 549 nm with emission at 590 nm for MitoTracker Orange and excitation at 306 nm with emission at 405 nm for Hoescht. Images were analyzed using ImageJ and fusogenicity quantified as mitochondrial aspect ratio (length/width), and were indexed to the maximal response elicited by Compound 35, a known mitofusin activator. Response curves were interpolated using the sigmoidal model using Prism 8 software. $EC_{50}$ values are reported as mean with 95% confidence limits for at least 3 independent experiments.

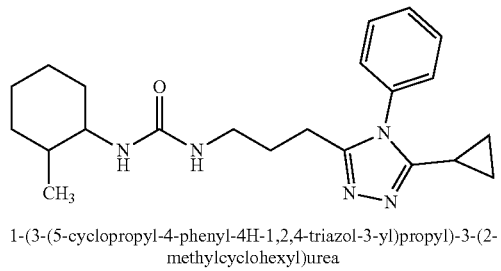

Compound 35

1-(3-(5-cyclopropyl-4-phenyl-4H-1,2,4-triazol-3-yl)propyl)-3-(2-methylcyclohexyl)urea In vitro pharmacokinetic analyses were performed in duplicate using standard methods by WuXi AppTec Co. Ltd. (Shanghai, China). Plasma protein binding was measured by equilibrium dialysis; % bound=(1−[free compound in dialysate]/[total compound in retentate])×100. Plasma stability of 2 uM compounds in clarified freeze-thawed plasma was assessed by LC-MS/MS of supernatants after protein precipitation; 120 min data are reported for studies including 0, 10, 30, 60, and 120 min. Liver microsome stability of 1 uM compounds in liver microsomes (0.5 mg/ml) after 0, 5, 10, 20, 30, 60 min. incubation was assessed by LC/MS/MS of reaction extracts.

Passive artificial blood brain barrier membrane permeability assay (PAMPA-BBB) were performed using 150 μL of 10 μM compounds (5% DMSO) added to PVDF membranes pre-coated with 5 μL of 1% brain polar lipid extract (Porcine)/dodecane mixture and incubated for 4 h at room temperature with shaking at 300 rpm. Donor and acceptor samples were analyzed by LC-MS/MS.

Further testing details for the MFN activity and PAMPA are provided in U.S. Patent Applications 2020/0345668 and 2020/0345669, incorporated herein by reference above.

Synthesis of N-(trans-4-hydroxycyclohexyl)-5-phenylpentanamide (Formula 1). This mitofusin activator was prepared as described in U.S. Patent Application Publication 2020/0345668, incorporated by reference above. This compound was used as a reference standard in activity testing below.

Synthesis of 1-(4-hydroxypiperidin-1-yl)-7-phenyl-heptan-1-one (Formula 7)

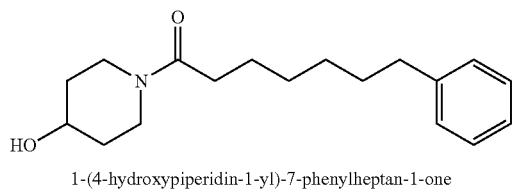

Formula 7

1-(4-hydroxypiperidin-1-yl)-7-phenylheptan-1-one

To a solution of 7-phenylheptanoic acid (100 mg, 484 μmol) in DMF (1.00 mL) was added HOBt (78.6 mg, 581 μmol), EDCI (139 mg, 727 μmol) and DIEA (125 mg, 969 μmol, 168 μL). Piperidin-4-ol (53.9 mg, 533 mol) was added and stirred at 25° C. for 16 h. The mixture was purified by HPLC (column: Phenomenex Gemini-NX C18 75×30 mm×3 μm; mobile phase: [water (0.1% TFA)-ACN]; B %: 45%-55%, 7 min). After HPLC purification, the residue was adjusted to pH=7 with saturated sodium bicarbonate solution and extracted with EtOAc (20.0 mL×2). The combined organic layers were dried over Na$_2$SO$_4$ and concentrated under vacuum at 40° C., and the residue was combined with H$_2$O (20.0 mL) and ACN (2.50 mL). The mixture was lyophilized to obtain the title compound (31.1 mg, 106 umol, 22.1% yield, 99.5% purity) as a yellow oil. LC-MS: Rt=0.868 min, m/z=290.1(M+H). HPLC: Rt=1.983 min, 99.5% purity under 220 nm. $^1$H NMR: 400 MHz CDCl$_3$ δ: 7.26-7.30 (m, 2H), 7.16-7.19 (m, 3H), 4.08-4.14 (m, 1H), 3.92-3.94 (m, 1H), 3.70-3.76 (m, 1H), 3.14-3.23 (m, 2H), 2.59-2.63 (m, 2H), 2.30-2.34 (m, 2H), 1.86-1.89 (m, 2H), 1.55-1.62 (m, 4H), 1.46-1.53 (m, 2H), 1.35-1.39 (m, 4H). $^{13}$C NMR: 400 MHz CDCl$_3$ δ: (171, 142, 128, 125, 77.3, 77.2, 76.7, 67.3, 42.8, 38.8, 35.8, 34.6, 34.0, 33.3, 31.3, 29.3, 29.0, 25.3) ppm.

Synthesis of 1-(3-hydroxypiperidin-1-yl)-7-phenyl-heptan-1-one (Formula 8)

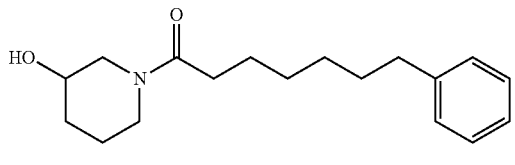

1-(3-hydroxypiperidin-1-yl)-7-phenylheptan-1-one

To a solution of 7-phenylheptanoic acid (100 mg, 484 μmol) in DMF (1.00 mL) was added HOBt (78.6 mg, 581 μmol), EDCI (139 mg, 727 μmol) and DIEA (125 mg, 969 μmol, 168 μL). Piperidin-3-ol (53.9 mg, 533 μmol) was added to the mixture and stirred at 25° C. for 16 h. The mixture was then purified by HPLC (column: Phenomenex Gemini-NX C18 75×30 mm×3 um; mobile phase: [water (0.1% TFA)-ACN]; B %: 48%-58%, 7 min). The residue was adjusted to pH=7 with saturated sodium bicarbonate solution and extracted with EtOAc (20.0 mL×3). The combined organic layers were dried over Na$_2$SO$_4$, concentrated under vacuum at 45° C., and combined with H$_2$O (20.0 mL) and ACN (2.50 mL). The mixture was lyophilized to give the title compound (35.5 mg, 121 μmol, 25.2% yield, 99.4% purity) as a light yellow oil. LC-MS: Rt=0.876 min, m/z=290.2 (M+H)–. HPLC: Rt=2.018 min, 99.4% purity under 220 nm. $^1$H NMR: 400 MHz MeOD-d4 δ: 7.20-7.28 (m, 2H), 7.10-7.18 (m, 3H), 3.62-3.70 (m, 2H), 3.23-3.29 (m, 1H), 3.15-3.21 (m, 1H), 2.60 (t, J=7.6 Hz, 2H), 2.35-2.40 (m, 2H), 1.90-1.95 (m, 1H), 1.75-1.83 (m, 1H), 1.36-1.64 (m, 11H). $^{13}$C NMR: 400 MHz MeOD-d4 δ: (174, 144, 129, 126, 67.3, 53.7, 47.3, 43.3, 36.9, 34.3, 33.8, 33.5, 32.7, 30.4, 30.2, 26.6, 24.7, 23.3) ppm.

Synthesis of 1-(4-hydroxypiperidin-1-yl)-6-phenyl-hexan-1-one (Formula 9)

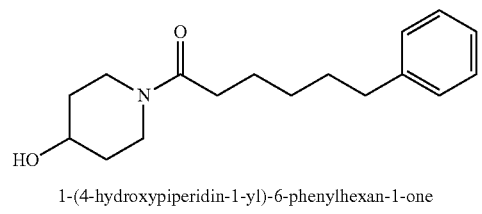

1-(4-hydroxypiperidin-1-yl)-6-phenylhexan-1-one

To a solution of 6-phenylhexanoic acid (100 mg, 520 μmol, 98.0 μL) in DMF (1.00 mL) was added HOBt (84.3 mg, 624 μmol), DIEA (134 mg, 1.04 mmol, 181 μL), EDCI (150 mg, 780 μmol) and piperidin-4-ol (57.9 mg, 572 μmol). The mixture was stirred at 30° C. for 16 h and was purified by HPLC (column: Phenomenex Gemini-NX C18 75×30 mm×3 um; mobile phase: [water (0.1% TFA)-ACN]; B %: 38%-48%, 7 min). The residue was adjusted to pH=7 with saturated sodium bicarbonate solution and extracted with EtOAc (20.0 mL×3). The combined organic layers were dried over Na$_2$SO$_4$ and concentrated under reduced pressure to give a residue, and the residue was combined with H$_2$O (15 mL) and ACN (5.0 mL). The mixture was lyophilized to obtain the title compound (49.2 mg, 178 μmol, 34.3% yield, 99.8% purity) as a white solid. LC-MS: Rt=0.836 min, m/z=276.1(M+H). HPLC: Rt=1.854 min, 99.8% purity under 220 nm. $^1$H NMR: 400 MHz CDC$_3$δ: 7.27-7.31 (m, 2H), 7.18-7.20 (m, 3H), 4.09-4.13 (m, 1H), 3.92-3.95 (m, 1H), 3.71-3.91 (m, 1H), 3.17-3.21 (m, 2H), 2.61-2.65 (m, 2H), 2.31-2.35 (m, 2H), 1.87-1.89 (m, 3H), 1.67-1.69 (m, 4H), 1.64-1.65 (m, 2H), 1.40-1.42 (m, 2H). $^{13}$C NMR: 400 MHz CDCl$_3$ δ: (171, 143, 128, 126, 67.2, 42.8, 38.9, 35.7, 34.6, 33.9, 33.2, 31.2, 29.1, 25.2) ppm.

Synthesis of 1-(4-hydroxypiperidin-1-yl)-8-pheny-loctan-1-one (Formula 10)

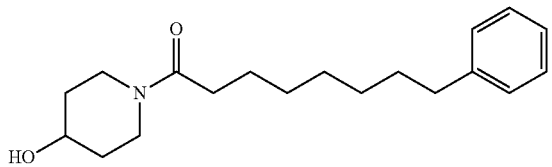

1-(4-hydroxypiperidin-1-yl)-8-phenyloctan-1-one

To a solution of 8-phenyloctanoic acid (100 mg, 453 μmol) in DMF (1.00 mL) was added HOBt (73.6 mg, 544.6 μmol), EDCI (130 mg, 680 μmol), DIEA (117 mg, 907 μmol, 158 μL) and piperidin-4-ol (53.9 mg, 533 μmol). The mixture was stirred at 30° C. for 3.5 h and purified by HPLC (column: Phenomenex Gemini-NX C18 75×30 mm×3 μm; mobile phase: [water (0.1% TFA)-ACN]; B %: 52%-62%, 7 min). The residue was adjusted to pH=7 with saturated sodium bicarbonate solution and extracted with EtOAc (20 mL×3). The combined organic layers were dried over Na$_2$SO$_4$, concentrated under reduced pressure to give a residue, and combined with H₂O (10 mL) and ACN (1.00 mL). The mixture was then lyophilized to give the title compound (45.2 mg, 146 µmol, 32.3% yield, 98.4% purity) as an off-white solid. LC-MS: Rt=0.885 min, m/z=304.2 (M+H)+. HPLC: Rt=2.111 min, 98.4% purity under 220 nm. ¹H NMR: 400 MHz MeOD δ: 7.2-7.25 (m, 2H), 7.11-7.17 (m, 3H), 4.05-4.08 (m, 1H), 3.78-3.86 (m, 2H), 3.26-3.29 (m, 1H), 3.11-3.12 (m, 1H), 2.58-2.62 (m, 2H), 2.36-2.40 (m, 2H), 1.56-1.63 (m, 2H), 1.38-1.39 (m, 4H), 1.33-1.36 (m, 8H). ¹³C NMR: 400 MHz MeOD δ: 174, 144, 130, 127, 67.9, 44.6, 40.5, 37.0, 35.8, 35.0, 34.2, 32.8, 30.5, 30.3, 26.8) ppm.

Synthesis of 4-hydroxy-N-(5-phenylpentyl)piperidine-1-carboxamide (Formula 18)

Formula 18

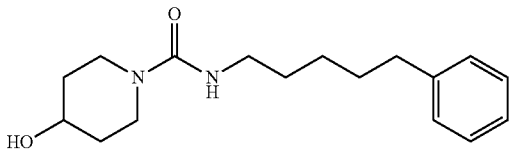

4-hydroxy-N-(5-phenylpentyl)piperidine-1-carboxamide

To a solution of 5-phenylpentan-1-amine (100 mg, 500 µmol, HCl) in DMF (1.0 mL) was added CDI (97.4 mg, 600 µmol) and TEA (152 mg, 1.50 mmol, 209 µL). The mixture was degassed and purged with N₂ 3 times and stirred at 30° C. for 0.5 h under N₂. Piperidin-4-ol (60.7 mg, 600 µmol) was added and stirred at 30° C. for 16 h under N₂. The mixture was diluted with H₂O (15 mL) and extracted with EtOAc (15 mL×3). The combined organic layers were washed with brine (10 mL×3), dried over Na₂SO₄, filtered, and concentrated under reduced pressure to give a residue. The residue was purified by HPLC (column: Waters Xbridge C18 150×50 mm×10 µm; mobile phase: [water (10 mM NH₄HCO₃)-ACN]; B %: 20%-50%, 10 min) to obtain the title compound (44.8 mg, 151 µmol, 30.2% yield, 98.0% purity) as an off-white solid. LCMS: Rt=0.860 min, m/z=291.3 (M+H)+. HPLC: Rt=2.165 min, 98.1% purity under 220 nm. ¹H NMR: 400 MHz MeOD-d4 δ: 7.25-7.13 (m, 5H), 3.79-3.75 (m, 3H), 3.14-3.11 (m, 2H), 3.03-2.99 (m, 2H), 2.63-2.59 (m, 2H), 1.80-1.66 (m, 2H), 1.64-1.62 (m, 2H), 1.52-1.41 (m, 2H), 1.38-1.34 (m, 4H). ¹³C NMR: 400 MHz MeOD-d4 δ: 160, 143, 130, 129, 127, 68.4, 42.8, 41.9, 36.9, 35.1, 32.6, 31.3, 27.6) ppm.

Synthesis of 4-hydroxy-N-(5-phenylpentyl)cyclohexane-1-carboxamide (Formula 26)

Formula 26

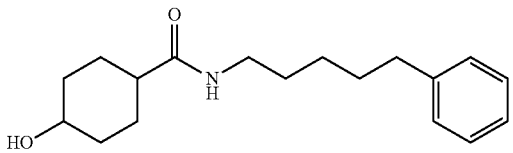

4-hydroxy-N-(5-phenylpentyl)cyclohexane-1-carboxamide

To a solution of 4-hydroxycyclohexane-1-carboxylic acid (32.8 mg, 227 µmol) in DMF (1.0 mL) was added HOBt (36.9 mg, 273 µmol), EDCI (65.4 mg, 341 µmol), DIEA (88.2 mg, 682 µmol, 118 µL) and 5-phenylpentan-1-amine (50.0 mg, 250 µmol, HCl). The mixture was stirred at 30° C. for 16 h and purified by HPLC (column: Phenomenex Gemini-NX C18 75×30 mm×3 µm; mobile phase: [water (0.1% TFA)-ACN]; B %: 40%-50%, 7 min). The title compound (44.0 mg, 150 µmol, 66.0% yield, 98.7% purity) was obtained as an off-white solid. LC-MS: Rt=0.847 min, m/z=290.1 (M+H)–. HPLC: Rt=1.881 min, Rt=1.922 min, 98.7% purity under 220 nm. ¹H NMR: 400 MHz MeOD-d4 δ: 7.25-7.11 (m, 5H), 3.91-3.47 (m, 1H), 3.17-3.13 (m, 2H), 2.62-2.59 (m, 2H), 1.99-1.97 (m, 1H), 1.76-1.65 (m, 2H), 1.63-1.61 (m, 2H), 1.53-1.50 (m, 2H), 1.49-1.34 (m, 5H), 1.33-1.20 (m, 3H). ¹³C NMR: 400 MHz MeOD-d4 δ: (179, 178, 143, 130, 129, 126, 70.7, 66.6, 45.6, 45.4, 40.2, 36.9, 35.7, 32.9, 32.5, 32.4, 30.4, 30.3, 29.2, 27.5, 24.9) ppm.

Synthesis of (1r,4r)-4-hydroxy-N-(4-phenylbutoxy)cyclohexane-1-carboxamide (Formula 28A, diastereomer of Formula 28)

Formula 28A

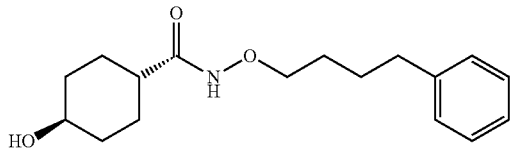

(1r,4r)-4-hydroxy-N-(4-phenylbutoxy)cyclohexane-1-carboxamide

To a mixture of (4-bromobutyl)benzene (300 mg, 1.41 mmol) and 2-hydroxyisoindoline-1,3-dione (275 mg, 1.69 mmol) in DMF (10.00 mL) was added K₂CO₃ (389 mg, 2.82 mmol) at 20° C. The mixture was stirred at 80° C. for 1 hr to obtain (191 mg, 646 µmol, 45.9% yield). To a solution of 2-(4-phenylbutoxy)isoindoline-1,3-dione (190 mg, 643 µmol) in DCM (10.0 mL) was added NH₂—NH₂·H₂O (322 mg, 6.43 mmol) at 25° C. The mixture was stirred for 2 hrs to obtain O-(4-phenylbutyl)hydroxylamine (95.0 mg, 574 µmol, 89.3% yield). The O-(4-phenylbutyl)hydroxylamine was combined with (1r,4r)-4-hydroxycyclohexane-1-carboxylic acid (124 mg, 862 µmol) in THF (10.0 mL), along with HATU (327 mg, 862 µmol) and TEA (174 mg, 1.72 mmol, 3.00 mL) at 25° C. The mixture was stirred at 25° C. for 2 hrs. The reaction mixture was concentrated under reduced pressure to give a residue. The reside was purified by HPLC (neutral condition, column: Waters Xbridge 150× 25 mm×5 µm; mobile phase: [water (10 mM NH₄HCO₃)-ACN]; B %: 26%-56%, 10 min). The title compound (83.72 mg, 286 µmol, 49.7% yield, 99.6% purity) was obtained as an off-white solid. LCMS: RT=0.730 min, m/z=292.2 (M+H)+. HPLC: RT=1.803 mins, 99.6% purity under 220 nm. ¹H NMR: 400 MHz, DMSO-d₆ δ: 10.9-10.5 (m, 1H), 7.28-7.25 (m, 2H), 7.19-7.14 (m, 3H), 4.63-4.52 (m, 1H), 3.73-3.70 (m, 2H), 3.34-3.30 (m, 1H), 2.59-2.56 (m, 2H), 1.84-1.81 (m, 3H), 1.64-1.62 (m, 4H), 1.60-1.51 (m, 2H), 1.43-1.28 (m, 2H), 1.09-1.06 (m, 2H).

Synthesis of (1r,4R)-4-hydroxy-N-((1R,2R)-2-(3-phenylpropyl)cyclopropyl)cyclohexane-1-carboxamide (Formula 29A, diastereomer of Formula 29)

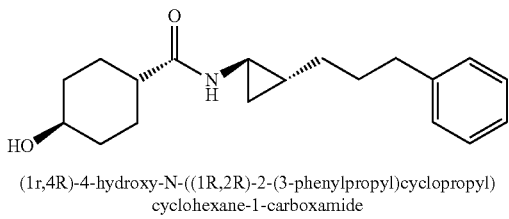

Formula 29A (1r,4R)-4-hydroxy-N-((1R,2R)-2-(3-phenylpropyl)cyclopropyl)cyclohexane-1-carboxamide To a solution of 4-phenylbutanal (3.34 g, 22.5 mmol) was added tert-butyl 2-(triphenyl-15-phosphaneylidene)acetate (10.1 g, 27.0 mmol) under $N_2$ at 25° C. The mixture was stirred for 12 hrs to obtain tert-butyl (E)-6-phenylhex-2-enoate (3.54 g, 14.3 mol, 63.7% yield). To a mixture of BLAHmethane iodide [$(CH_3)_3SOI$] (1.61 g, 7.31 mmol) in DMSO (10.0 mL) was added NaH (292 mg, 7.31 mmol) at 25° C. under $N_2$, and the mixture was stirred at 25° C. for 1 hr. After 1 hr, tert-butyl (E)-6-phenylhex-2-enoate (1.50 g, 6.09 mmol) was added to the mixture, which was stirred another 1 hr to obtain tert-butyl (1S,2S)-2-(3-phenylpropyl)cyclopropane-1-carboxylate (790 mg, 3.03 mmol, 49.8% yield). To a mixture of tert-butyl (1S,2S)-2-(3-phenylpropyl)cyclopropane-1-carboxylate (790 mg, 3.03 mmol) in DCM (10.0 mL) was added TFA (14.1 g, 124 mmol, 9.19 mL) at 25° C. and stirred for 1 hr to obtain (1S,2S)-2-(3-phenylpropyl)cyclopropane-1-carboxylic acid (576 mg, 2.82 mmol, 92.9% yield). To a mixture of (1S,2S)-2-(3-phenylpropyl)cyclopropane-1-carboxylic acid (576 mg, 2.82 mmol) in toluene (10.0 mL) was added DPPA (776 mg, 2.82 mmol), TEA (428 mg, 4.23 mmol) at 25° C. under $N_2$. The mixture was heated to 105° C. and stirred for 2 hrs to obtain (1S,2S)-2-(3-phenylpropyl)cyclopropan-1-amine (73.0 mg, 416 μmol, 14.7% yield). To a mixture of (1S,2S)-2-(3-phenylpropyl)cyclopropan-1-amine (73.0 mg, 416 μmol) and (1r,4r)-4-hydroxycyclohexane-1-carboxylic acid (72.1 mg, 500 μmol) in THF (10.0 mL) was added HATU (237 mg, 625 μmol) and TEA (361 mg, 3.57 mmol, 0.50 mL) at 25° C. and stirred for 12 hrs. The reaction mixture was concentrated under reduced pressure to give a residue, and purified by HPLC (TFA condition, column: Phenomenex Synergi Polar-RP 100×25 mm×4 μm; mobile phase: [water (TFA)-ACN]; B %: 43%-63%, 7 min) to obtain the title compound (8.29 mg, 26.6 μmol, 6.38% yield, 96.6% purity) as a white solid. LCMS: RT=0.892 min, m/z=302.2 (M+H)+. HPLC: RT=2.309 mins, 96.6% purity under 220 nm. $^1H$ NMR: 400 MHz, DMSO-$d_6$δ: 7.72 (d, J=4.0, 1H), 7.28-7.24 (m, 2H), 7.19-7.13 (m, 3H), 4.51 (d, J=4.4, 1H), 3.30-3.26 (m, 1H), 2.60-2.56 (m, 2H), 2.32-2.27 (m, 1H), 1.83-1.79 (m, 3H), 1.65-1.60 (m, 4H), 1.34-1.30 (m, 2H), 1.20-1.19 (m, 2H), 1.07-1.04 (m, 2H), 0.75-0.70 (m, 1H), 0.51-0.49 (m, 1H), 0.38-0.36 (m, 1H).

Synthesis of (1r,4r)-4-hydroxy-N-(2-(4-phenylbutyl)cyclopropyl)cyclohexane-1-carboxamide (Formula 30A, diastereomer of Formula 30)

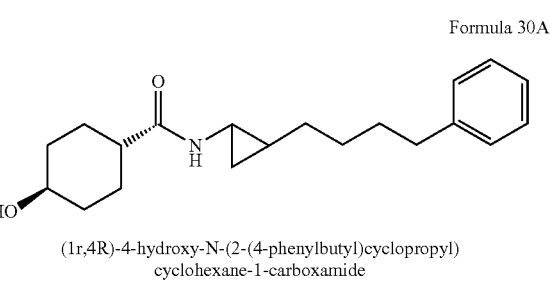

Formula 30A (1r,4R)-4-hydroxy-N-(2-(4-phenylbutyl)cyclopropyl)cyclohexane-1-carboxamide The title compound was synthesized as outlined in Scheme 1.

Scheme 1

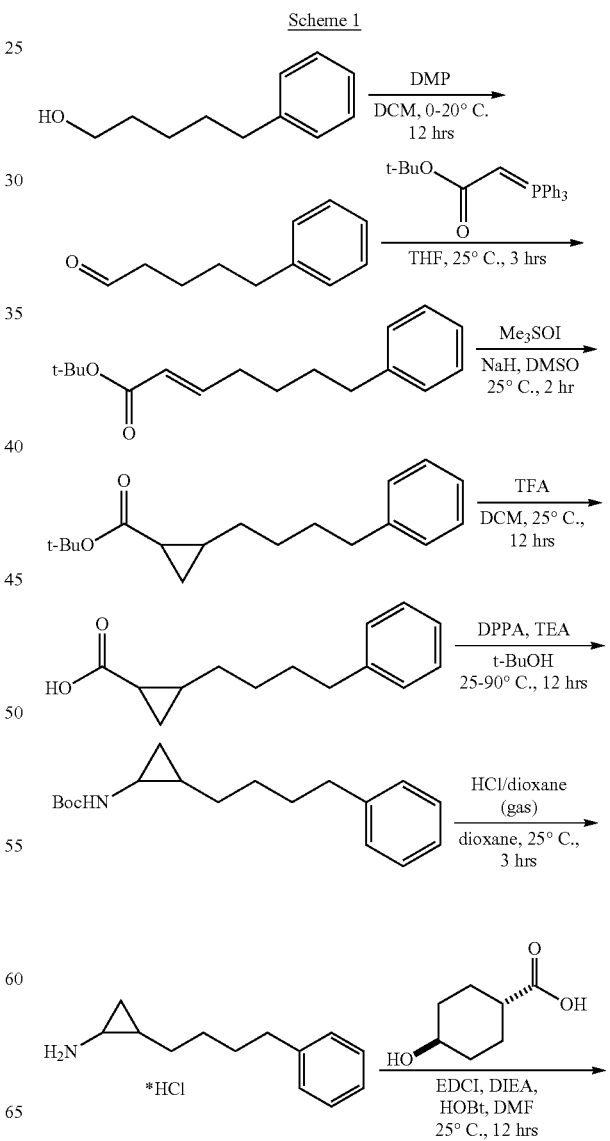

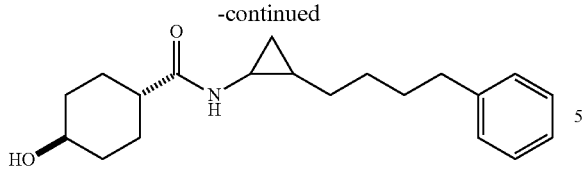

Formula 30A

In brief, 5-phenylpentan-1-ol was converted to the corresponding aldehyde using Dess-Martin periodinane, and the crude aldehyde was then converted to the corresponding t-butyl-α,β-unsaturated ester using tert-butyl 2-(triphenyl-l5-phosphaneylidene)acetate in ~75% overall yield. Cyclopropanation was then conducted using Me₃SOI in ~36% overall yield. The t-butyl ester was cleaved using trifluoroacetic acid, and the crude cyclopropyl carboxylic was then converted to the corresponding BOC-protected amine in ~48% overall yield using diphenylphosphoryl azide in t-butanol. The free amine was liberated in ~91% yield using HCl gas in dioxane, which was then coupled with (1r,4r)-4-hydroxycyclohexane-1-carboxylic acid using EDCI to afford the title compound in 50% yield. LCMS: RT=0.521 min, m/z=316.2 (M+H)+. HPLC: RT=2.738 mins, 96.2% purity under 220 nm. ¹H NMR: 400 MHz, DMSO-d₆δ: 7.69 (d, J=4.4 Hz, 1H), 7.27-7.24 (m, 2H), 7.18-7.13 (m, 3H), 4.51 (d, J=4.4 Hz, 1H), 3.30-3.26 (m, 1H), 2.57-2.53 (m, 2H), 2.32-2.31 (m, 1H), 1.89-1.80 (m, 3H), 1.63-1.57 (m, 4H), 1.37-1.31 (m, 6H), 1.08-1.04 (m, 2H), 0.70-0.68 (m, 1H), 0.48-0.46 (dt, J=8.8, 4.8 Hz, 1H), 0.37-0.36 (m, 1H).

Synthesis of (1r,4r)-4-hydroxy-N-(3-(3-phenylpropyl)cyclobutyl)cyclohexane-1-carboxamide (Formula 31A, diastereomer of Formula 31)

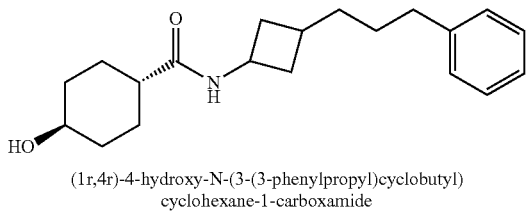

Formula 31A (1r,4r)-4-hydroxy-N-(3-(3-phenylpropyl)cyclobutyl)cyclohexane-1-carboxamide The title compound was synthesized in a similar manner to Formula 30A, except producing 3-(3-phenylpropyl)cyclobutan-1-amine as the intermediate for coupling. The identity of the product was confirmed by LC-MS, HPLC, and ¹H NMR.

Synthesis of (1r,4S)-4-hydroxy-N-((1S,2S)-2-phenethoxycyclopropyl)cyclohexane-1-carboxamide (Formula 32A, diastereomer of Formula 32)

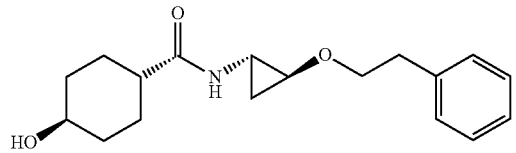

Formula 32A (1r,4S)-4-hydroxy-N-((1S,2S)-2-(3-phenethoxycyclopropyl)cyclohexane-1-carboxamide To a mixture of ethyl (1S,2S)-2-phenethoxycyclopropane-1-carboxylate (440 mg, 1.88 mmol) in MeOH (5.00 mL), THF (5.00 mL) and H₂O (2.00 mL) was added LiOH·H₂O (157 mg, 3.76 mmol) at 25° C. The mixture was heated to 70° C. and stirred for 2 hrs to obtain (1S,2S)-2-phenethoxycyclopropane-1-carboxylic acid (284 mg, 1.38 mmol, 73.3% yield). To a mixture of (1S,2S)-2-phenethoxycyclopropane-1-carboxylic acid (264 mg, 1.28 mmol) in toluene (10.0 mL) was added DPPA (352 mg, 1.28 mmol) and TFA (194 mg, 1.92 mmol, 1.50 eq) at 25° C. under N₂. The mixture was heated to 105° C. and stirred for 2 hrs to obtain (1S,2S)-2-phenethoxycyclopropan-1-amine (54.0 mg, 304 μmol, 23.8% yield). To a mixture of (1S,2S)-2-phenethoxycyclopropan-1-amine (47.0 mg, 265 μmol) and (1r,4r)-4-hydroxycyclohexane-1-carboxylic acid (45.8 mg, 318 μmol) in THF (10.0 mL) was added HATU (151 mg, 397 μmol) and TEA (727 mg, 7.18 mmol, 1.00 mL) at 25° C. and stirred for 12 hrs. The reaction mixture was concentrated under reduced pressure to give a residue and purified by HPLC (neutral condition, column: Waters Xbridge 150× 25 mm×5 μm; mobile phase: [water (NH₄HCO₃)-ACN]; B %: 25%-55%, 10 min and TFA condition, and column: Phenomenex Synergi Polar-RP 100×25 mm×4 μm; mobile phase: [water (TFA)-ACN]; B %: 36%-56%, 7 min) to obtain the title compound (7.89 mg, 25.7 μmol, 9.69% yield, 98.8% purity) as a white solid. LCMS: RT=0.716 min, m/z=304.2 (M+H)+. HPLC: RT=1.709 mins, 98.8% purity under 220 nm. ¹H NMR: 400 MHz, DMSO-d₆δ: 7.74 (d, J=3.6, 1H), 7.29-7.25 (m, 2H), 7.23-7.16 (m, 3H), 4.55 (d, J=4.4, 1H), 3.77-3.66 (m, 2H), 3.33-3.29 (m, 2H), 3.07-3.06 (m, 1H), 2.81-2.77 (m, 2H), 1.88-1.79 (m, 3H), 1.64-1.60 (m, 2H), 1.33-1.30 (m, 2H), 1.13-1.07 (m, 2H), 0.84-0.82 (m, 1H), 0.65-0.64 (m, 2H).

Synthesis of (1r,4r)-N-(2-(benzyloxy)cyclopropyl)-4-hydroxycyclohexane-1-carboxamide (Formula 33A, diastereomer of Formula 33)

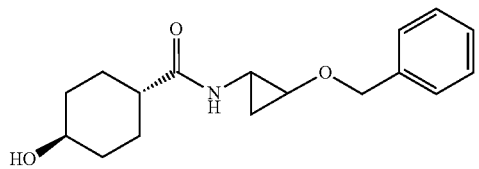

Formula 33A (1r,4r)-N-(2-(benzyloxy)cyclopropyl)-4-hydroxycyclohexane-1-carboxamide To a mixture of ethyl 2-(benzyloxy)cyclopropane-1-carboxylate (750 mg, 3.41 mmol) in MeOH (5.00 mL), THF (5.00 mL) and H$_2$O (2.00 mL) was added LiOH·H$_2$O (285 mg, 6.81 mmol) at 25° C. The mixture was heated to 70° C. and stirred for 2 hrs to obtain 2-(benzyloxy)cyclopropane-1-carboxylic acid (485 mg, 2.52 mmol, 74.1% yield). To a mixture of 2-(benzyloxy)cyclopropane-1-carboxylic acid (485 mg, 2.52 mmol) in toluene (10.0 mL) was added DPPA (694 mg, 2.52 mmol), TFA (382 mg, 3.78 mmol) at 25° C. under N$_2$. The mixture was heated to 105° C. and stirred for 2 hrs to obtain 2-(benzyloxy)cyclopropan-1-amine (108 mg, 661 μmol, 26.2% yield). To a mixture of 2-(benzyloxy)cyclopropan-1-amine (108 mg, 661 μmol) and (1r,4)-4-hydroxycyclohexane-1-carboxylic acid (114 mg, 794 μmol) in THF (10.0 mL) was added HATU (377 mg, 992 μmol) and TEA (1.81 g, 17.9 mmol, 2.50 mL) at 25° C. and stirred for 12 hrs. The reaction mixture was concentrated under reduced pressure to give a residue and purified by HPLC (TFA condition column: Phenomenex Synergi Polar-RP 100×25 mm×4 μm; mobile phase: [water (TFA)-ACN]; B %: 32%-52%, 7 min) and (neutral condition, column: Waters Xbridge 150×25 mm×5 μm; mobile phase: [water (NH$_4$HCO$_3$)-ACN]; B %: 21%-51%, 9 min) to obtain the title compound (5.97 mg, 20.1 umol, 3.05% yield, 97.8% purity) as a white solid. LCMS: RT=0.671 min, m/z=290.1 (M+H)+. HPLC: RT=1.821 mins, 97.8% purity under 220 nm. $^1$H NMR: 400 MHz, DMSO-d$_6$δ: 7.76 (d, J=3.2, 1H), 7.26-7.30 (m, 5H), 4.62-4.53 (m, 3H), 3.31-3.29 (m, 1H), 3.14-3.12 (m, 1H), 2.64-2.63 (m, 1H), 1.91-1.80 (m, 3H), 1.64-1.62 (m, 2H), 1.36-1.33 (m, 2H), 1.09-1.05 (m, 2H), 1.01-0.97 (m, 1H), 0.71-0.70 (m, 1H).

Synthesis of (1r,4r)-4-hydroxy-N-(2-(3-phenyl-propoxy)cyclopropyl)cyclohexane-1-carboxamide (Formula 34A, diastereomer of Formula 34)

Formula 34A

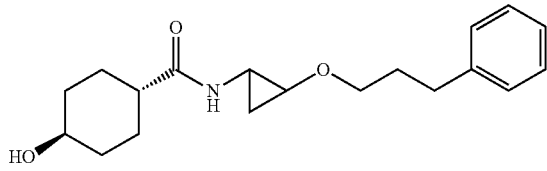

(1r,4r)-4-hydroxy-N-(2-(3-phenylpropoxy)cyclopropyl) cyclohexane-1-carboxamide

To a mixture of ethyl 2-(3-phenylpropoxy)cyclopropane-1-carboxylate (870 mg, 3.50 mmol) in MeOH (5.00 mL), THF (5.00 mL) and H$_2$O (2.00 mL) was added LiOH·H$_2$O (294 mg, 7.01 mmol) at 25° C. The mixture was heated to 70° C. and stirred for 2 hrs to obtain 2-(3-phenylpropoxy) cyclopropane-1-carboxylic acid (690 mg, 3.13 mmol, 89.4% yield). To a mixture of 2-(3-phenylpropoxy)cyclopropane-1-carboxylic acid (690 mg, 3.13 mmol) in toluene (10.0 mL) was added DPPA (862 mg, 3.13 mmol), TFA (475 mg, 4.70 mmol) at 25° C. under N$_2$. The mixture was heated to 105° C. and stirred for 2 hrs to obtain 2-(3-phenylpropoxy) cyclopropan-1-amine (154 mg, 805 μmol, 25.7% yield). To a mixture of 2-(3-phenylpropoxy)cyclopropan-1-amine (154 mg, 805 μmol) and (1r,4r)-4-hydroxycyclohexane-1-carboxylic acid (139 mg, 966 μmol) in THF (5.00 mL) was added HATU (459 mg, 1.21 mmol) and TEA (727 mg, 7.18 mmol, 1.00 mL) at 25° C. and stirred for 12 hrs. The reaction mixture was concentrated under reduced pressure to give a residue and purified by HPLC (TFA condition column: Phenomenex Synergi Polar-RP 100×25 mm×4 μm; mobile phase: [water (TFA)-ACN]; B %: 41%-61%, 7 min) and (neutral condition, column: Waters Xbridge 150×25 mm×5 μm; mobile phase: [water (NH$_4$HCO$_3$)-ACN]; B %: 31%-61%, 10 min) to obtain the title compound (7.29 mg, 22.5 μmol, 2.80% yield, 98.1% purity) as an off-white solid. LCMS: RT=0.830 min, m/z=318.2 (M+H)+. HPLC: RT=1.814 mins, 98.1% purity under 220 nm. $^1$H NMR: 400 MHz, DMSO-d$_6$δ: 7.71 (d, J=3.6, 1H), 7.28-7.25 (m, 2H), 7.19-7.16 (m, 3H), 4.52 (d, J=4.4, 1H), 3.54-3.45 (m, 2H), 3.43-3.30 (m, 1H), 3.07-3.06 (m, 1H), 2.59-2.55 (m, 3H), 1.89-1.82 (m, 1H), 1.80-1.76 (m, 4H), 1.73-1.61 (m, 2H), 1.34-1.30 (m, 2H), 1.08-1.05 (m, 2H), 0.90-0.87 (m, 1H), 0.65-0.64 (m, 1H).

Mitofusin Activity and In Vitro Pharmacology. Table 1 below summarizes the biological activity of compounds having Formulas 7-10, 18, 24, 26, 28A, and 29A-34A in comparison to the mitofusin activator having Formula 1.

TABLE 1

| Formula | EC$_{50}$ (nm) | Plasma Protein Binding (Bound %) | | Liver Microsomes (t$_{1/2}$, minutes) | | PAMPA (10$^{-6}$ cm/s) |
|---|---|---|---|---|---|---|
| | | Human | Mouse | Human | Mouse | |
| 1 (Comparative) | 8.42 | 91 | 96.3 | >145 | 92.4 | 26.277 |
| 7 | 30.5 | 95.1 | 95.7 | 103.3 | 52.5 | 145.127 |
| 8 | >10000 | 96.6 | 95.9 | 60.6 | 22.5 | 180.027 |
| 9 | >10000 | 83.7 | 91.2 | >145 | 82.4 | 96.106 |
| 10 | 12.16 | 98.6 | 98.9 | 64.5 | 28 | 142.782 |
| 18 | 3.85 | 91.7 | 91.6 | 133.6 | 94.8 | 14.585 |
| 26 | 9.68 | 89.3 | 92.9 | >145 | 102.1 | 30.249 |
| 28A | ND | 68.51 | unstable | 10.3 | 3.8 | 10.1 |
| 29A | >10000 | 89.13 | 95.34 | >145 | 77.8 | 50.9 |
| 30A | 5.3 | 95.3 | 96.8 | 139 | 193 | 86.8 |
| 31A | 9 | 95.8 | 97.1 | 110 | 224 | 95.1 |
| 32A | 10.54 | 46.48 | 72.14 | >145 | >145 | 5.43 |
| 33A | 10.82 | 37.36 | 63.93 | >145 | >145 | 2.28 |
| 34A | 26.69 | 62.95 | 77.92 | >145 | >145 | 10.5 |

As shown, compounds having Formulas 7-10 and containing the amide nitrogen atom bonded endocyclically exhibited an unexpectedly sharp increase in PAMPA values compared to the compound having Formula 1. Some of these compounds also maintained low EC$_{50}$ values comparable to those of the compound having Formula 1. The corresponding urea analogue of the compound having Formula 7 (i.e., the urea compound having Formula 18) exhibited an order of magnitude decrease (improvement) in EC$_{50}$ but also a corresponding decrease in its PAMPA value. The corresponding amide analogue having the amide nitrogen atom located on the other side of the carbonyl group (i.e., the amide having Formula 26) exhibited EC$_{50}$ and PAMPA values that remained similar to those of the compound having Formula 1. Compounds having Formulas 28A-34A, each containing modifications of the linker between the amide nitrogen atom and the phenyl group in the compound having Formula 26, maintained low EC$_{50}$ in some cases but did not improve upon the PAMPA assay value, except for compounds having Formulas 30A and 31A.

Unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents

What is claimed is the following:

1. A composition comprising:
   a mitofusin activator having a structure represented by

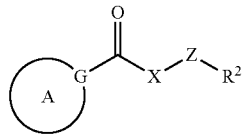

any stereoisomer thereof, or any pharmaceutically acceptable salt thereof;
   wherein:
   G is CH, and A is an optionally substituted 5- or 6-membered cycloalkyl or heterocycloalkyl ring;
   X is NR$^1$Cyc;
      wherein R$^1$ is H or C$_1$-C$_6$ alkyl, and Cyc is 1,2-cyclopropyl, 1,2-cyclobutyl, 1,3-cyclobutyl, 1,2-cyclopentyl, 1,3-cyclopentyl, 1,2-cyclohexyl, 1,3-cyclohexyl, or 1,4-cyclohexyl;
   Z is $(CH_2)_4$ or $(CH_2)_{n_1}O(CH_2)_{n_2}$;
      wherein $n_1$ is an integer ranging from 0 to 3, $n_2$ is an integer ranging from 0 to 3, and $n_1+n_2$ ranges from 1 to 3; and
   R$^2$ is an optionally substituted phenyl aryl or heteroaryl group.

2. The composition of claim 1, wherein A represents an optionally substituted piperidinyl, pyrrolidinyl, tetrahydropyranyl, tetrahydrofuranyl, cyclopentyl, or cyclohexyl group.

3. The composition of claim 2, wherein the mitofusin activator has a structure represented by

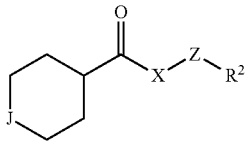

or any stereoisomer thereof;
      wherein J is a bond, CH(hal), CHOR$^3$, CHR$^4$, CHNR$^4$R$^5$, O, or NR$^4$;
         wherein hal is a halogen, R$^3$ is H or C$_1$-C$_6$ alkyl, and R$^4$ and R$^5$ are independently H, C$_1$-C$_6$ alkyl, or C$_1$-C$_6$ acyl.

4. The composition of claim 2, wherein X is NR$^1$ (1,2-cyclopropyl).

5. The composition of claim 4, wherein Z is $(CH_2)_4$, $O(CH_2)$, $O(CH_2)_2$, or $O(CH_2)_3$.

6. The composition of claim 4, wherein A is 4-hydroxycyclohexyl.

7. The composition of claim 2, wherein the mitofusin activator has a structure represented by

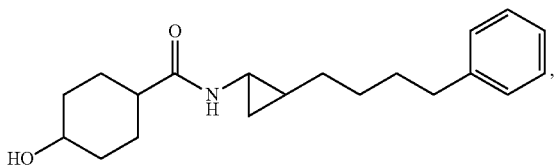

4-hydroxy-N-(2-(4-phenylbutyl)cyclopropyl)cyclohexane-1-carboxamide

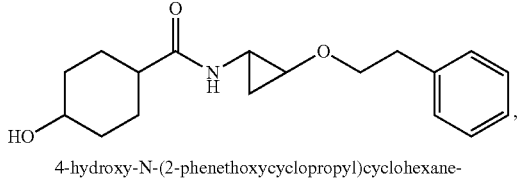

4-hydroxy-N-(2-phenethoxycyclopropyl)cyclohexane-1-carboxamide

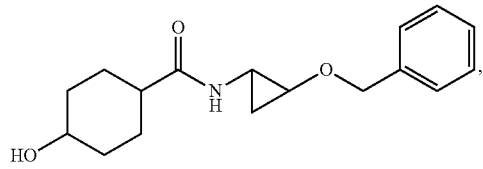

N-(2-(benzyloxy)cyclopropyl)-4-hydroxycyclohexane-1-carboxamide

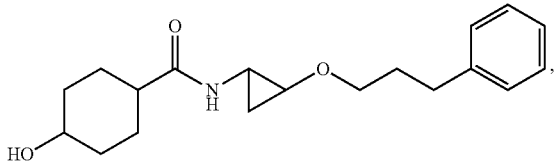

4-hydroxy-N-(2-(3-phenylpropoxy)cyclopropyl)cyclohexane-1-carboxamide or any stereoisomer thereof.

8. The composition of claim 1, further comprising: a pharmaceutically acceptable excipient.

9. A composition comprising:
a mitofusin activator having a structure represented by

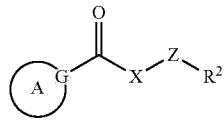

any stereoisomer thereof, or any pharmaceutically acceptable salt thereof; wherein:
G is CH, and A is an optionally substituted 5- or 6-membered cycloalkyl or heterocycloalkyl ring;
X is NR$^1$Cyc;
wherein R$^1$ is H or C$_1$-C$_6$ alkyl, and Cyc is 1,2-cyclopropyl;
Z is (CH$_2$)$_4$; and
R$^2$ is an optionally substituted aryl or heteroaryl group.

10. The composition of claim 9, wherein R$^2$ is an optionally substituted phenyl group.

11. The composition of claim 10, wherein A represents an optionally substituted piperidinyl, pyrrolidinyl, tetrahydropyranyl, tetrahydrofuranyl, cyclopentyl, or cyclohexyl group.

12. The composition of claim 11, wherein the mitofusin activator has a structure represented by

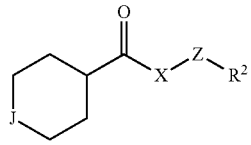

or any stereoisomer thereof;
wherein J is a bond, CH (hal), CHOR$^3$, CHR$^4$, CHNR$^4$R$^5$, O, or NR$^4$;
wherein hal is a halogen, R$^3$ is H or C$_1$-C$_6$ alkyl, and R$^4$ and R$^5$ are independently H, C$_1$-C$_6$ alkyl, or C$_1$-C$_6$ acyl.

13. The composition of claim 12, wherein J is CHOR$^3$ or CHR$^4$.

14. The composition of claim 9, wherein A represents an optionally substituted piperidinyl, pyrrolidinyl, tetrahydropyranyl, tetrahydrofuranyl, cyclopentyl, or cyclohexyl group.

15. The composition of claim 14, wherein the mitofusin activator has a structure represented by

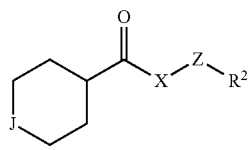

or any stereoisomer thereof;
wherein J is a bond, CH (hal), CHOR$^3$, CHR$^4$, CHNR$^4$R$^5$, O, or NR$^4$;
wherein hal is a halogen, R$^3$ is H or C$_1$-C$_6$ alkyl, and R$^4$ and R$^5$ are independently H, C$_1$-C$_6$ alkyl, or C$_1$-C$_6$ acyl.

16. The composition of claim 15, wherein J is CHOR$^3$ or CHR$^4$.

17. The composition of claim 9, wherein A is 4-hydroxycyclohexyl.

18. The composition of claim 9, wherein the wherein the mitofusin activator has a structure represented by

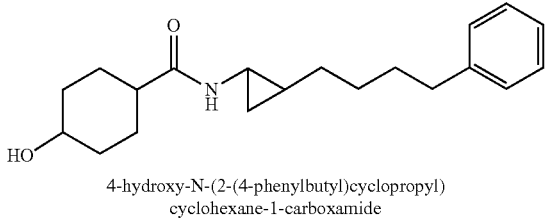

4-hydroxy-N-(2-(4-phenylbutyl)cyclopropyl)cyclohexane-1-carboxamide.

19. A composition comprising: a mitofusin activator having a structure represented by

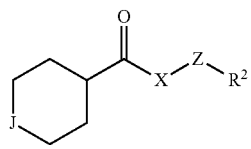

any stereoisomer thereof, or any pharmaceutically acceptable salt thereof;
wherein:
X is $NR^1Cyc$;
wherein $R^1$ is H or $C_1$-$C_6$ alkyl, and Cyc is 1,2-cyclopropyl, 1,2-cyclobutyl, 1,3-cyclobutyl, 1,2-cyclopentyl, 1,3-cyclopentyl, 1,2-cyclohexyl, 1,3-cyclohexyl, or 1,4-cyclohexyl;
Z is $(CH_2)_4$ or $(CH_2)_{n_1}O(CH_2)_{n_2}$;
wherein $n_1$ is an integer ranging from 0 to 3, $n_2$ is an integer ranging from 0 to 3, and $n_1+n_2$ ranges from 1 to 3; and
$R^2$ is an optionally substituted aryl or heteroaryl group;
wherein J is $CHOR^3$ or $CHR^4$, $R^3$ is H or $C_1$-$C_6$ alkyl, and $R^4$ is H, $C_1$-$C_6$ alkyl, or $C_1$-$C_6$ acyl.

* * * * *